(12) United States Patent
Lautenschlager et al.

(10) Patent No.: US 12,295,957 B2
(45) Date of Patent: *May 13, 2025

(54) ASCORBIC ACID AND QUINONE COMPOUNDS IN COMBINATION WITH AN ANTIPARASITIC AGENT FOR TREATING A PARASITIC DISEASE

(71) Applicant: IC-MedTech Corp., Las Vegas, NV (US)

(72) Inventors: Sueli de Oliveira Silva Lautenschlager, Maringa (BR); Vania Cristina Desoti, Palotina (BR); Celso Vataru Nakamura, Maringa (BR); Valdecir Farias Ximenes, Bauru (BR)

(73) Assignee: IC-MedTech Corp., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/412,805

(22) Filed: Jan. 15, 2024

(65) Prior Publication Data
US 2024/0165084 A1    May 23, 2024

Related U.S. Application Data

(63) Continuation of application No. 16/972,004, filed as application No. PCT/US2019/035501 on Jun. 5, 2019, now Pat. No. 11,872,233.
(Continued)

(51) Int. Cl.
*A61K 31/541*    (2006.01)
*A61K 9/00*    (2006.01)
(Continued)

(52) U.S. Cl.
CPC .......... *A61K 31/541* (2013.01); *A61K 9/0056* (2013.01); *A61K 31/122* (2013.01);
(Continued)

(58) Field of Classification Search
CPC .. A61K 31/541; A61K 9/0056; A61K 31/122; A61K 31/345; A61K 31/375;
(Continued)

(56) References Cited

U.S. PATENT DOCUMENTS 6,468,414 B1    10/2002    Mahdavi et al.
7,091,241 B2    8/2006    Gilloteaux et al.
(Continued)

FOREIGN PATENT DOCUMENTS

WO    2009035908 A1    3/2009
WO    2009063044 A1    5/2009
(Continued)

OTHER PUBLICATIONS

Akiyoshi et al., "The potential of vitamin K3 as an anticancer agent against breast cancer that acts via the mitochondria-related apoptotic pathway," Cancer Chemother. Pharmacol. 2009, 65, 143-50.
(Continued)

*Primary Examiner* — Taylor V Oh
(74) *Attorney, Agent, or Firm* — Lin Yu; Juniv LLP

(57) ABSTRACT

Provided herein is a method of treating, preventing, or alleviating one or more symptoms of *Chagas disease* in a subject, comprising administering to the subject: (i) ascorbic acid, or a single enantiomer, a mixture of enantiomers, or a mixture of diastereomers thereof; or a pharmaceutically acceptable salt, solvate, or hydrate thereof; (ii) a quinone compound, or a single enantiomer, a mixture of enantiomers, or a mixture of diastereomers thereof, or a pharmaceutically acceptable salt, solvate, hydrate, or prodrug thereof; and (iii) an antiparasitic agent.

20 Claims, 6 Drawing Sheets

Related U.S. Application Data

(60) Provisional application No. 62/681,500, filed on Jun. 6, 2018.

(51) Int. Cl.
  *A61K 31/122* (2006.01)
  *A61K 31/345* (2006.01)
  *A61K 31/375* (2006.01)
  *A61K 31/4168* (2006.01)
  *A61K 31/4184* (2006.01)
  *A61K 45/06* (2006.01)
  *A61P 33/00* (2006.01)

(52) U.S. Cl.
  CPC .......... *A61K 31/345* (2013.01); *A61K 31/375* (2013.01); *A61K 31/4168* (2013.01); *A61K 31/4184* (2013.01); *A61K 45/06* (2013.01); *A61P 33/00* (2018.01)

(58) Field of Classification Search
  CPC ............ A61K 31/4168; A61K 31/4184; A61K 45/06; A61K 9/08; A61K 47/22; A61P 33/00; A61P 17/02; Y02A 50/30
  USPC ........................................................ 514/394
  See application file for complete search history.

(56) References Cited

U.S. PATENT DOCUMENTS

| | | | |
|---|---|---|---|
| 8,507,555 | B2 | 8/2013 | Miller et al. |
| 11,872,233 | B2* | 1/2024 | Lautenschlager .. A61K 31/4168 |
| 2012/0184609 | A1 | 7/2012 | Jamison et al. |
| 2013/0178522 | A1 | 7/2013 | Jamison et al. |
| 2013/0219528 | A1 | 8/2013 | Borgström |
| 2014/0200270 | A1 | 7/2014 | Masyuk et al. |

FOREIGN PATENT DOCUMENTS

| | | |
|---|---|---|
| WO | 2018026673 A1 | 2/2018 |
| WO | 2019236656 A1 | 12/2019 |

OTHER PUBLICATIONS

Ariyanayagam et al., "Bis(glutathionyl)spermine and other novel trypanothione analogues in Trypanosoma cruzi," J. Biol. Chem. 2003, 278, 27612-9.
Bana et al., "A novel coumarin-quinone derivative SV37 inhibits CDC25 phosphatases, impairs proliferation, and induces cell death," Mol. Carcinog. 2015, 54, 229-41.
Beck et al., "Ascorbate/menadione-induced oxidative stress kills cancer cells that express normal or mutated forms of the oncogenic protein Bcr-Abl. An in vitro and in vivo mechanistic study," Invest. New Drugs 2011, 29, 891-900.
Benites et al., "An in vitro comparative study with furyl-1,4-quinones endowed with anticancer activities," Invest. New Drugs 2011, 29, 760-7.
Blommaart et al., "The phosphatidylinositol 3-kinase inhibitors wortmannin and LY294002 inhibit autophagy in isolated rat hepatocytes," Eur. J. Biochem. 1997, 243, 240-6.
Bothiraja et al., "Development of plumbagin-loaded phospholipid-Tween® 80 mixed micelles: formulation, optimization, effect on breast cancer cells and human blood/serum compatibility testing," Ther. Deliv. 2013, 4, 1247-59.
Boveris et al., "Superoxide anion production and trypanocidal action of naphthoquinones on Trypanosoma cruzi," Comp. Biochem. Physiol. C. 1978, 61, 327-9.
Brandy et al., "Synthesis and characterization of novel unsymmetrical and symmetrical 3-halo- or 3-methoxy-substituted 2-dibenzoylamino-1,4-naphthoquinone derivatives," Molecules 2013, 18, 1973-84.

Brener et al., "Therapeutic activity and criterion of cure on mice experimentally infected with Trypanosoma cruzi," Rev. Inst. Med. Trop. Sao Paulo 1962, 4, 389-96.
Caballero et al., "In vitro and in vivo antiparasital activity against Trypanosoma cruzi of three novel 5-methyl-1,2,4-triazolo[1,5-a]pyrimidin-7(4H)-one-based complexes," J. Inorg. Biochem. 2011, 105, 770-6.
Camargo, "Growth and differentiation in Trypanosoma cruzi. Origen of metacyclic trypanosomes in liquid media," Rev. Inst. Med. Trop. São Paulo 1964, 6, 93-100.
Castro et al., "In vitro and in vivo evaluation of anti-Trypanosoma cruzi activity of derivates of vitamin K," Sociedade Brasileira de Medicina Tropical, 2012, p. 1.
Castro et al., "Toxic side effects of drugs used to treat Chagas' disease (American trypanosomiasis)," Hum. Exp. Toxicol. 2006, 25, 471-9.
Chou et al., "Quantitative analysis of dose-effect relationships: the combined effects of multiple drugs or enzyme inhibitors," Adv. Enzyme Regul. 1984, 22, 27-55.
Ciccarelli et al., "Antiparasitic effect of vitamin B12 on Trypanosoma cruzi," Antimicrob. Agents Chemother. 2012, 56, 5315-20.
Coura et al., "A critical review on Chagas disease chemotherapy," Mem. Inst. Oswaldo Cruz. 2002, 97, 3-24.
Croft et al., "The activity of hydroxynaphthoquinones against Leishmania donovani " J. Antimicrob. Chemother. 1992, 30, 827-32.
Dahl et al., "A protein kinase antigenically related to pp60v-src possibly involved in yeast cell cycle control: positive in vivo regulation by sterol," Proc. Natl. Acad. Sci. U.S.A. 1987, 84, 4012-6.
Desoti et al., "The combination of vitamin K3 and vitamin C has synergic activity against forms of trypanosoma cruzi through a redox imbalance process," PLoS One 2015, 10, e0144033.
Desoti et al., "Trypanocidal action of (-)-elatol involves an oxidative stress triggered by mitochondria dysfunction," Mar. Drugs 2012,10, 1631-46.
Docampo et al., "Enhancement of the cytotoxicity of crystal violet against Trypanosoma cruzi in the blood by ascorbate," Mol. Biochem. Parasitol. 1988, 27, 241-7.
Elingold et al., "Mechanism of action of novel naphthofuranquinones on rat liver microsomal peroxidation," Chem. Biol. Interact. 2009, 182, 213-9.
Faundez et al., "Buthionine sulfoximine increases the toxicity of nifurtimox and benznidazole to Trypanosoma cruzi," Antimicrob. Agents Chemother. 2005, 49, 126-30.
Fleury et al., "Mitochondrial reactive oxygen species in cell death signaling," Biochimie 2002, 84, 131-41.
Ghobadifar et al., "The role of benznidazole with cyanocobalamin and ascorbic acid in treating the chronic phase of Chagas disease," Rev. Soc. Bras. Med. Trop. 2014, 47, 669.
Gilloteaux et al., "Autoschizis: a new form of cell death for human ovarian carcinoma cells following ascorbate: menadione treatment. Nuclear and DNA degradation," Tissue Cell. 2004, 36, 197-209.
Gilloteaux et al., "Cancer cell necrosis by autoschizis: synergism of antitumor activity of vitamin C: vitamin K3 on human bladder carcinoma T24 cells," Scanning 1998, 20, 564-75.
Gilloteaux et al., "Cell damage and death by autoschizis in human bladder (RT4) carcinoma cells resulting from treatment with ascorbate and menadione," Ultrastruct. Pathol. 2010, 34, 140-60.
Gilloteaux et al., "Cell death by autoschizis in TRAMP prostate carcinoma cells as a result of treatment by ascorbate: menadione combination," Ultrastruct. Pathol. 2005, 29, 221-35.
Graciani and Ximenes, "2-Bromo-1,4-naphthoquinone: a potentially improved substitute of menadione in Apatone ™ therapy," Braz. J. Med. Biol. Res. 2012, 45, 701-10.
Haberzettl et al., "Oxidized lipids activate autophagy in a JNK-dependent manner by stimulating the endoplasmic reticulum stress response," Redox Biol. 2013, 1, 56-64.
Ibrahim et al., "Antioxidant therapy against Trypanosome infections: A Review Update," Curr. Top Med. Chem. 2016, 16, 2233-44.
Irigoín et al., "Insights into the redox biology of Trypanosoma cruzi: trypanothione metabolism and oxidant detoxification," Free Radic. Biol. Med. 2008, 45, 733-42.

(56) References Cited

OTHER PUBLICATIONS

Izumi et al., "Natural products and Chagas' disease: a review of plants compounds studied for activity against Trypanosoma cruzi," Nat. Prod. Rep. 2011, 28, 809-23.
Jamison et al., "Autoschizis: a novel cell death," Biochem. Pharm. 2002, 63, 1773-83.
Jamison et al., "Cell cycle arrest and autoschizis in a human bladder carcinoma cell line following vitamin C and vitamin K3 treatment," Biochem. Pharmacol. 2004, 67, 337-51.
Jamison et al., "The role of nutrition in preventing and treating breast and prostate cancer: evaluation of the in vitro and in vivo antitumor activities of vitamin C and K-3 combinations against human prostate cancer," J. Nutr. 2001, 131, 158S-60S.
Jannin and Villa, "An overview of Chagas disease treatment," Mem. Inst. Oswaldo Cruz. 2007, 102 Suppl. 1, 95-7.
Lamson et al., "The anticancer effects of vitamin K," Altern. Med. Rev. 2003, 8, 303-18.
Lanzarin-Bidoia et al., "Further evidence of the trypanocidal action of eupomatenoid-5: Confirmation of involvement of reactive oxygen species and mitochondria owing to a reduction in trypanothione reductase activity," Free Radic. Biol. Med. 2013, 60, 17-28.
Maçao et al., "Antioxidant therapy attenuates oxidative stress in chronic cardiopathy associated with Chagas' disease," Int. J. Cardiol. 2007, 123, 43-9.
Maguire, "Chagas' disease—Can we stop the deaths?" N. Engl. J. Med. 2006, 355, 760-1.
Marim et al., "Effects of vitamin C supplementation on acute phase Chagas disease in experimentally infected mice with Trypanosoma cruzi QM1 strain," Rev. Inst. Med. Trop. Sao Paulo 2012, 54, 319-23.
Márquez et al., "Redox metabolism in Trypanosoma cruzi. Biochemical characterization of dithiol glutaredoxin dependent cellular pathways," Biochimie 2014, 106, 56-67.
Maya et al., "Mode of action of natural and synthetic drugs against Trypanosoma cruzi and their interaction with the mammalian host," Comp. Biochem. Physiol. A Mol. Integr. Physiol. 2007, 146, 601-20.
Menna-Barreto et al., "The effects on Trypanosoma cruzi of novel synthetic naphthoquinones is mediated by mitochondrial dysfunction," Free Radic. Biol. Med. 2009, 47, 644-53.
Munafo et al., "A novel assay to study autophagy: regulation of autophagosome vacuole size by amino acid deprivation," J. Cell Sci. 2001, 114, 3619-29.
Noto et al., "Effects of sodium ascorbate (vitamin C) and 2-methyl-1,4-naphthoquinone (vitamin K3) treatment on human tumor cell growth in vitro. I. Synergism of combined vitamin C and K3 action," Cancer 1989, 63, 901-6.
Orrenius et al., "Mitochondrial oxidative stress: implications for cell death," Annu. Rev. Pharmacol. Toxicol. 2007, 47, 143-83.
Padhye et al., "Perspectives on medicinal properties of plumbagin and its analogs," Med. Res. Rev. 2012, 32, 1131-58.
Pelizzaro-Rocha et al., "Synergistic effects of parthenolide and benznidazole on Trypanosoma cruzi," Phytomedicine 2010, 18, 36-9.
Piacenza et al., "Enzymes of the antioxidant network as novel determiners of Trypanosoma cruzi virulence," Int. J. Parasitol. 2009, 39, 1455-64.
Pinto et al., "The trypanocidal activity of naphthoquinones: a review," Molecules 2009,14, 4570-90.
Polanco-Hernández et al., "Synergistic effect of lupenone and caryophyllene oxide against Trypanosoma cruzi," Evid. Based Complement. Alternat. Med. 2013, 2013, 1-6.
Pompella et al., "Measurement of lipid peroxidation in vivo: a comparison of different procedures," Lipids 1987, 22, 206-11.
Ramirez-Macias et al., "Taiwaniaquinoid and abietane quinone derivatives with trypanocidal activity against T. cruzi and Leishmania spp," Parasitol. Int. 2012, 61, 405-13.
Rodrigues et al., "A quinoxaline derivative as a potent chemotherapeutic agent, alone or in combination with benznidazole, against Trypanosoma cruzi," PLoS One 2014, 9, e85702.
Salmon-Chemin et al., "2- and 3-Substituted 1,4-naphthoquinone derivatives as subversive substrates of trypanothione reductase and lipoamide dehydrogenase from Trypanosoma cruzi: synthesis and correlation between redox cycling activities and in vitro cytotoxicity," J. Med. Chem. 2001, 44, 548-65.
Salomão et al., "Trypanosoma cruzi mitochondrial swelling and membrane potential collapse as primary evidence of the mode of action of naphthoquinone analogues," BMC Microbiol. 2013, 13, 1-12.
Shukla et al., "Iridoid glucosides from Nyctanthes arbortristis result in increased reactive oxygen species and cellular redox homeostasis imbalance in Leishmania parasite," Eur. J. Med. Chem. 2012, 54, 49-58.
Silva et al., "Synthesis and biological activity against Trypanosoma cruzi of substituted 1,4-naphthoquinones," Eur. J. Med. Chem. 2013, 60, 51-6.
Taper et al., "In vivo reactivation of DNases in implanted human prostate tumors after administration of a vitamin C/K(3) combination," J. Histochem. Cytochem. 2001, 49, 109-19.
Tareen et al., "A 12 week, open label, phase I/IIa study using Apatone for the treatment of prostate cancer patients who have failed standard therapy," Int. J. Med. Sci. 2008, 5, 62-7.
Tarleton et al., "The challenges of Chagas disease-grim outlook or glimmer of hope?" PLoS Med. 2007, 4, e332.
Uc-Cachon et al., "Naphthoquinones isolated from Diospyros anisandra exhibit potent activity against pan-resistant first-line drugs Mycobacterium tuberculosis strains," Pulm. Pharmacol. Ther. 2014, 27, 114-20.
Venugopal et al., "Synergistic antitumour activity of vitamins C and K3 against human prostate carcinoma cell lines," Cell Biol. Int. 1996, 20, 787-97.
Verrax et al., "Ascorbate potentiates the cytotoxicity of menadione leading to an oxidative stress that kills cancer cells by a non-apoptotic caspase-3 independent form of cell death," Apoptosis 2004, 9, 223-33.
Verrax et al., "Oxidative stress by ascorbate/menadione association kills K562 human chronic myelogenous leukaemia cells and inhibits its tumour growth in nude mice," Biochem. Pharmacol. 2006, 72, 671-80.
Verrax et al., "The association of vitamins C and K3 kills cancer cells mainly by autoschizis, a novel form of cell death. Basis for their potential use as coadjuvants in anticancer therapy," Eur. J. Med. Chem. 2003, 38, 451-7.
Weinstein et al., "Modeling the impact of drug interactions on therapeutic selectivity," Nat. Commun. 2018, 9, 3452.
Who Chagas disease (American trypanosomiasis) Fact sheet No. 340, Jun. 2010.
Wilkinson et al., "Distinct mitochondrial and cytosolic enzymes mediate trypanothione-dependent peroxide metabolism in Trypanosoma cruzi," J. Biol. Chem. 2000, 275, 8220-5.
Wilkinson et al., "Vitamin C biosynthesis in trypanosomes: A role for the glycosome," Proc. Natl. Acad. Sci. U.S.A. 2005, 102, 11645-50.
Wu et al., "Vitamin K3 induces cell cycle arrest and cell death by inhibiting Cdc25 phosphatase," Eur. J. Cancer 1999, 35, 1388-93.
Wymann et al., "Wortmannin inactivates phosphoinositide 3-kinase by covalent modification of Lys-802, a residue involved in the phosphate transfer reaction," Mol. Cell. Biol. 1996, 16, 1722-33.
Zhao et al., "Comparison of methods for evaluating drug-drug interaction," Front. Biosci. 2010, 2, 241-9.

\* cited by examiner

ASCORBIC ACID AND QUINONE COMPOUNDS IN COMBINATION WITH AN ANTIPARASITIC AGENT FOR TREATING A PARASITIC DISEASE

CROSS REFERENCE TO RELATED APPLICATIONS

This application is a continuation of U.S. application Ser. No. 16/972,004, filed Dec. 4, 2020; which is a National Stage of International Application No. PCT/US2019/035501, filed Jun. 5, 2019; which claims the benefit of U.S. Provisional Application No. 62/681,500, filed Jun. 6, 2018; the disclosure of each of which is incorporated herein by reference in its entirety.

FIELD

Provided herein is a method of treating, preventing, or alleviating one or more symptoms of *Chagas disease* in a subject, comprising administering to the subject: (i) ascorbic acid, or a single enantiomer, a mixture of enantiomers, or a mixture of diastereomers thereof; or a pharmaceutically acceptable salt, solvate, or hydrate thereof; (ii) a quinone compound, or a single enantiomer, a mixture of enantiomers, or a mixture of diastereomers thereof, or a pharmaceutically acceptable salt, solvate, hydrate, or prodrug thereof; and (iii) an antiparasitic agent.

BACKGROUND

*Chagas disease*, also known as *American trypanosomiasis*, is a tropical parasitic disease caused by the protozoan *Trypanosoma cruzi*, affecting millions of people worldwide. World Health Organization. Chagas disease (*American trypanosomiasis*), WHO, Geneva, 2015. It is spread mostly by insects known as Triatominae or kissing bugs. Id. *Chagas disease* is considered a silent pathology since the first symptoms may appear several years after infection. Maguire, *N. Engl. J. Med.* 2006, 355, 760-761. The symptoms of *Chagas disease* change over the course of the infection. In the early stage, symptoms are typically either not present or mild, and may include fever, swollen lymph nodes, headaches, or local swelling at the site of the bite. After 8 to 12 weeks, individuals enter the chronic phase of the disease and in 60 to 70%, it never produces further symptoms. The other 30 to 40% of people develop further symptoms 10 to 30 years after the initial infection, including enlargement of the ventricles of the heart in 20 to 30%, leading to heart failure. An enlarged esophagus or an enlarged colon may also occur in 10% of people.

Currently, benznidazole and nifurtimox are only drugs available for treating *Chagas disease* and both were developed more than four decades ago. Coura et al., *Mem. Inst. Oswaldo Cruz.* 2002, 97, 3-24. Benznidazole and nifurtimox are also known to have variable efficacy and high toxicity. Id. For example, benznidazole and nifurtimox cause temporary side effects in up to 40% of people, including skin disorders, brain toxicity, and digestive system irritation. *Chagas disease* (*American trypanosomiasis*) Fact sheet No. 340. Therefore, there exists a need for an effective therapy for treating *Chagas disease*.

SUMMARY OF THE DISCLOSURE

Provided herein is a method of treating, preventing, or alleviating one or more symptoms of a parasitic disease in a subject, comprising administering to the subject: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

Also provided herein is a method of inhibiting parasitic growth in a subject infected with a parasite, comprising administering to the subject: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

Additionally provided herein is a method of eliminating a parasite from a subject, comprising administering to the subject: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

Furthermore, provided herein is a method of increasing the quality of life of a subject infected with a parasite, comprising administering to the subject: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

Provided herein is a method of increasing the efficacy of an antiparasitic agent in a subject infected with a parasite, comprising administering to the subject a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof.

Provided herein is a method of increasing tolerance to an antiparasitic agent in a subject infected with a parasite, comprising administering to the subject a therapeutically effective amount of: (i) vitamin C, or a pharmaceutically acceptable salt, solvate, or hydrate thereof; and (ii) a vitamin K compound, or a single enantiomer, a mixture of enantiomers, or a mixture of diastereomers thereof, or a pharmaceutically acceptable salt, solvate, hydrate, or prodrug thereof.

Provided herein is a method of reducing a side effect of an antiparasitic agent to a subject infected with a parasite, comprising administering to the subject a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof.

Provided herein is a method of reducing a toxicity of an antiparasitic agent to a subject infected with a parasite, comprising administering to the subject a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof.

Provided herein is a method of inhibiting parasitic growth, comprising contacting a parasite with: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

Provided herein is a method of killing a parasite, comprising contacting the parasite with: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

Provided herein is a method of increasing the cytotoxicity of an antiparasitic agent to a parasite, comprising contacting the parasite with: a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof.

DETAILED DESCRIPTION

Figure 1:
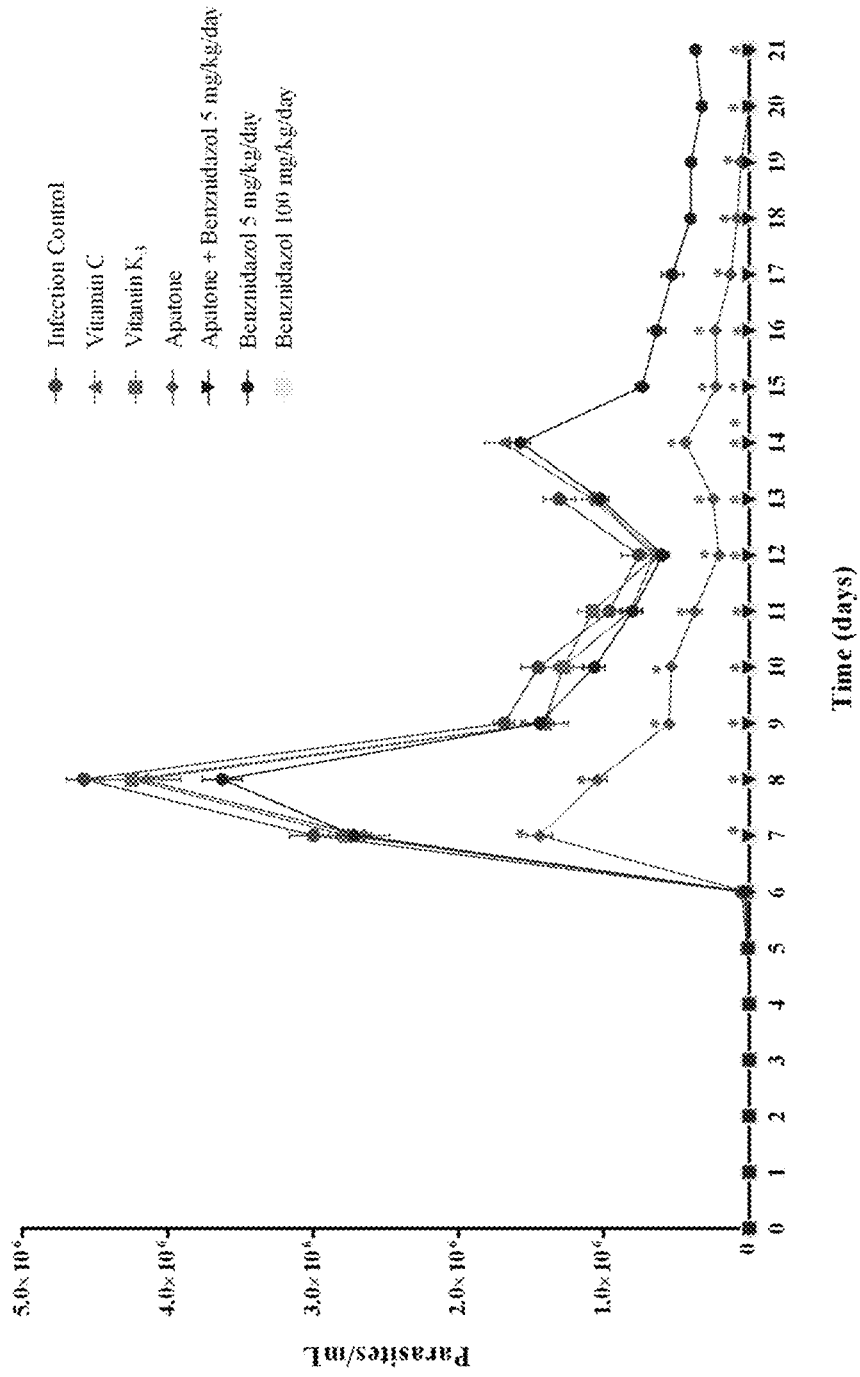
FIG. 1 shows the effects of vitamin C, vitamin $K_3$, APATONE®, and benznidazole on parasitemia in a murine model of *Chagas disease*, where the symbol * indicates a significant difference compared with the control group ($p \leq 0.05$).

To facilitate understanding of the disclosure set forth herein, a number of terms are defined below.

Generally, the nomenclature used herein and the laboratory procedures in organic chemistry, medicinal chemistry, biochemistry, biology, pharmacology, and others described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), livestock, a domestic pet, cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or one or more of its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The terms "therapeutically effective amount" and "effective amount" are meant to include the amount of a compound or a combination of compounds that, when administered, is sufficient to prevent development of, or alleviate to some extent, one or more of the symptoms of the disorder, disease, or condition being treated. The term "therapeutically effective amount" or "effective amount" also refers to the amount of a compound or a combination of compounds that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The terms "subtherapeutic amount" and "subtherapeutically effective amount" of a therapeutic agent are used interchangeably herein and refer to a dose lower than the amount which is effective when the therapeutic agent is delivered alone.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 22nd ed.; Allen et al., Eds.; *The Pharmaceutical Press,* 2012; *Handbook of Pharmaceutical Excipients,* 7th ed.; Rowe et al., Eds.; The Pharmaceutical Press: 2012; *Handbook of Pharmaceutical Additives,* 3rd ed.; Ash and Ash Eds.; Synapse Information Resources, Inc.: 2007; *Pharmaceutical Preformulation and Formulation,* 2nd ed.; Gibson Ed.; CRC Press LLC: 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer of a compound described herein.

The term "quality of life" or "QOL" refers to a maintenance or increase in a the overall physical and mental state of a subject, for example a subject infected with a parasite, such as the subject's cognitive ability, ability to communicate and interact with others, decreased dependence upon analgesics for pain control, maintenance of ambulatory ability, maintenance of appetite and body weight (lack of cachexia), lack of or diminished feeling of "hopelessness;" continued interest in playing a role in treatment, and other similar mental and physical states.

The term "alkyl" refers to a linear or branched saturated monovalent hydrocarbon radical, wherein the alkyl may optionally be substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and isopropyl), butyl (including all isomeric forms, e.g., n-butyl, isobutyl, sec-butyl, and t-butyl), pentyl (including all isomeric forms), and hexyl (including all isomeric forms).

The term "alkenyl" refers to a linear or branched monovalent hydrocarbon radical, which contains one or more, in one embodiment, one to five, in another embodiment, one, carbon-carbon double bond(s). The alkenyl may be optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s). The alkynyl may be optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl (—C≡CH), propynyl (including all isomeric forms, e.g., 1-propynyl (—C≡CCH3) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic saturated or non-aromatic unsaturated, bridged or non-bridged monovalent hydrocarbon radical, which is optionally substituted with one or more substituents Q as described herein. In certain embodiments, the cycloalkyl is a cyclic saturated bridged or non-bridged monovalent hydrocarbon radical. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "aryl" refers to a monocyclic aromatic group and/or multicyclic monovalent hydrocarbon aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. In certain embodiments, the term "aryl" refers to a bicyclic or tricyclic carbon ring, where one of the rings is aromatic and the others of which may be saturated, partially unsaturated, or aromatic, for example, dihydronaphthyl, indenyl, indanyl, or tetrahydronaphthyl (tetralinyl). In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-26}$), or from 7 to 16 ($C_{7-16}$) carbon atoms. Examples of aralkyl groups include, but are not limited to, benzyl, 1-phenylethyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each of which is independently selected from O, S, N, and P, in the ring. A heteroaryl group is bonded to the rest of a molecule through its aromatic ring. Each ring of a heteroaryl group can contain one or two 0 atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each of which is independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. A heterocyclyl group is bonded to the rest of a molecule through its non-aromatic ring. In certain embodiments, the heterocyclyl is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "halogen," "halide" or "halo" refers to fluorine, chlorine, bromine, and/or iodine.

The term "optionally substituted" is intended to mean that a group or substituent, such as an alkyl, alkenyl, alkynyl, cycloalkyl, aryl, aralkyl, heteroaryl, or heterocyclyl group, may be substituted with one or more substituents Q, each of which is independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (b) oxo (=O), halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) R$^b$ and R$^c$ together with the N atom to which they are attached form heteroaryl or heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each W, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, C$_{7-15}$ aralkyl, heteroaryl, or heterocyclyl; or (iii) R$^f$ and R$^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (—) are used to denote the optical rotation of the compound, that is, the direction in which a plane of polarized light is rotated by the optically active compound. The (—) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (—), is not related to the absolute configuration of the molecule, R and S.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "chromium-free" refers to a chemical (e.g., a compound or composition) that contains no more than 100 ppm, 50 ppm, 20 ppm, 10 ppm, 5 ppm, 2 ppm, 1 ppm, 0.1 ppm, 10 ppb, or 1 ppb of chromium. In one embodiment, the term "chromium-free" refers to a chemical that contains no more than 10 ppm of chromium. In another embodiment, the term "chromium-free" refers to a chemical that contains no more than 5 ppm of chromium. In yet another embodiment, the term "chromium-free" refers to a chemical that contains no more than 2 ppm of chromium. In still another embodiment, the term "chromium-free" refers to a chemical that contains no more than 1 ppm of chromium. The chromium content can be determined using a conventional technique well known to one of ordinary skill in the art, e.g., inductively coupled plasma (ICP) technique.

Ascorbic Acid Compounds

In one embodiment, the ascorbic acid compound is L-ascorbic acid or a pharmaceutically acceptable salt thereof; or a pharmaceutically acceptable solvate or hydrate thereof. L-Ascorbic acid is also known as vitamin C, L-xyloascorbic acid, 3-oxo-L-gulofuranolactone (enol form), L-3-ketothreohexuronic acid lactone, antiscorbutic vitamin, cevitamic acid, adenex, allercorb, ascorin, ascorteal, ascorvit, cantan, cantaxin, catavin C, cebicure, cebion, cecon, cegiolan, celaskon, celin, cenetone, cereon, cergona, cescorbat, cetamid, cetabe, cetemican, cevalin, cevatine, cevex, cevimin, ce-vi-sol, cevitan, cevitex, cewin, ciamin, cipca, concemin, C-vin, daviamon C, duoscorb, hybrin, laroscorbine, lemascorb, planavit C, proscorbin, redoxon, ribena, scorbacid, scorbu-C, testascorbic, vicelat, vitacee, vitacimin, vitacin, vitascorbol, and xitix.

In one embodiment, the ascorbic acid compound is L-ascorbic acid. In another embodiment, the ascorbic acid compound is a pharmaceutically acceptable salt of L-ascorbic acid, or a pharmaceutically acceptable solvate or hydrate thereof.

Suitable bases for forming a pharmaceutically acceptable salt of L-ascorbic acid include, but are not limited to, inorganic bases, such as magnesium hydroxide, calcium hydroxide, potassium hydroxide, zinc hydroxide, and sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

In one embodiment, the ascorbic acid compound is an alkali or alkaline earth metal salt of L-ascorbic acid, or a pharmaceutically acceptable solvate or hydrate thereof. In another embodiment, the ascorbic acid compound is sodium, potassium, calcium, or magnesium L-ascorbate, or a pharmaceutically acceptable solvate or hydrate thereof. In yet another embodiment, the ascorbic acid compound is sodium L-ascorbate, or a pharmaceutically acceptable solvate or hydrate thereof. In yet another embodiment, the ascorbic acid compound is sodium L-ascorbate, which is also known as vitamin C sodium, ascorbin, sodascorbate, natrascorb, cenolate, ascorbicin, or cebitate. In yet another embodiment, the ascorbic acid compound is potassium L-ascorbate, or a pharmaceutically acceptable solvate or hydrate thereof. In yet another embodiment, the ascorbic acid compound is calcium L-ascorbate, or a pharmaceutically acceptable solvate or hydrate thereof. In yet another embodiment, the ascorbic acid compound is calcium L-ascorbate. In yet another embodiment, the ascorbic acid compound is magnesium L-ascorbate, or a pharmaceutically acceptable solvate or hydrate thereof. In still another embodiment, the ascorbic acid compound is magnesium L-ascorbate.

In certain embodiments, the ascorbic acid compound is D-ascorbic acid or a pharmaceutically acceptable salt, or a pharmaceutically acceptable solvate or hydrate thereof.

In one embodiment, the ascorbic acid compound is D-ascorbic acid. In another embodiment, the ascorbic acid compound is a pharmaceutically acceptable salt of D-ascorbic acid, or a pharmaceutically acceptable solvate or hydrate thereof.

Suitable bases for forming a pharmaceutically acceptable salt of D-ascorbic acid include, but are not limited to, inorganic bases, such as magnesium hydroxide, calcium hydroxide, potassium hydroxide, zinc hydroxide, and sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

In one embodiment, the ascorbic acid compound is an alkali or alkaline earth metal salt of D-ascorbic acid, or a pharmaceutically acceptable solvate or hydrate thereof. In another embodiment, the ascorbic acid compound is sodium, potassium, calcium, or magnesium D-ascorbate, or a pharmaceutically acceptable solvate or hydrate thereof. In yet another embodiment, the ascorbic acid compound is sodium D-ascorbate, or a pharmaceutically acceptable solvate or hydrate thereof. In yet another embodiment, the ascorbic acid compound is sodium D-ascorbate, which is also known as vitamin C sodium, ascorbin, sodascorbate, natrascorb, cenolate, ascorbicin, or cebitate. In yet another embodiment, the ascorbic acid compound is potassium D-ascorbate, or a pharmaceutically acceptable solvate or hydrate thereof. In yet another embodiment, the ascorbic acid compound is calcium D-ascorbate, or a pharmaceutically acceptable solvate or hydrate thereof. In yet another embodiment, the ascorbic acid compound is calcium D-ascorbate. In yet another embodiment, the ascorbic acid compound is magnesium D-ascorbate, or a pharmaceutically acceptable solvate or hydrate thereof. In still another embodiment, the ascorbic acid compound is magnesium D-ascorbate.

In certain embodiments, the ascorbic acid compound is chromium-free. In certain embodiments, the chromium-free ascorbic acid compound contains no more than 100 ppm, 50 ppm, 20 ppm, 10 ppm, 5 ppm, 2 ppm, 1 ppm, 0.1 ppm, 10 ppb, or 1 ppb of chromium. In certain embodiments, the chromium-free ascorbic acid compound contains no greater than 10 ppm of chromium. In certain embodiments, the chromium-free ascorbic acid compound contains no greater than 5 ppm of chromium. In certain embodiments, the chromium-free ascorbic acid compound contains no greater than 2 ppm of chromium. In certain embodiments, the chromium-free ascorbic acid compound contains no greater than 1 ppm of chromium.

Quinone Compounds

In one embodiment, the quinone compound is vitamin K. In certain embodiments, the vitamin K is a 2-methyl-1,4-naphthoquinone of Formula I, II, or III:

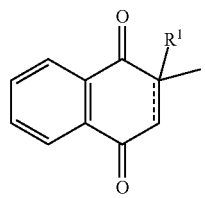

I

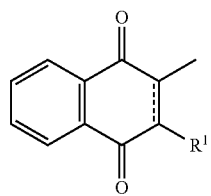

II

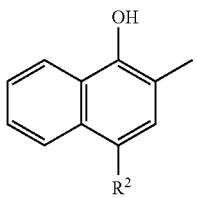

III or an enantiomer, a mixture of enantiomers, or a mixture of two or more diastereomers thereof; or a pharmaceutically acceptable salt, solvate, or hydrate thereof; wherein $R^1$ is $C_{1-20}$ alkyl, $C_{2-20}$ alkenyl, $C_{2-20}$ alkynyl, or —$SO_3H$; and $R^2$ is hydroxyl or amino.

In certain embodiments, the vitamin K is vitamin $K_1$, vitamin $K_2$, vitamin $K_3$, vitamin $K_4$, vitamin $K_5$, or a mixture of two or more thereof.

In one embodiment, the vitamin K is vitamin $K_1$, or a pharmaceutically acceptable salt, solvate, or hydrate thereof. Vitamin $K_1$ is also known as phylloquinone, [R-[R*,R*-(E)]]-2-methyl-3-(3,7,11,15-tetramethyl-2-hexadecenyl)-1,4-naphthalenedione, 2-methyl-3-phytyl-1,4-naphthoquinone, 3-phytylmenadione, phytomenadione, phytonadione, aqua-merphyton, konakion, mephyton, mono-day, veda-$K_1$, and veta-$K_1$.

In another embodiment, the vitamin K is vitamin $K_2$, or a pharmaceutically acceptable salt, solvate, or hydrate thereof. Vitamin $K_2$ is also known as menaquinones, and 2-methyl-3-all-trans-polyprenyl-1,4-naphthoquinones. Some non-limiting examples of vitamin $K_2$ include menaquinone 4, which is also known as vitamin $K_{2(20)}$; menaquinone 6, which is also known as vitamin $K_{2(30)}$; and menaquinone 7, which is also known as vitamin $K_{2(35)}$.

In yet another embodiment, the vitamin K is vitamin $K_3$, or a pharmaceutically acceptable salt, solvate, or hydrate thereof. Vitamin $K_3$ is also known as menadione, 2-methyl-1,4-naphthalenedione, 2-methyl-1,4-naphthoquinone, menaphthone, vitamin $K_2O$), kanone, kappaxin, kayklot, kayquinone, klottone, kolklot, thyloquinone, 1,2,3,4-tetrahydro-2-methyl-1,4-dioxo-2-naphthal enesulfonic acid, and sodium 1,2,3,4-tetrahydro-2-methyl-1,4-di oxo-2-naphthalenesulfonate. In certain embodiments, the vitamin K is menadione (i.e., 2-methyl-1,4-naphthal enedione).

In one embodiment, the vitamin K is 1,2,3,4-tetrahydro-2-methyl-1,4-dioxo-2-naphthalenesulfonic acid, or a pharmaceutically acceptable salt, solvate, or hydrate thereof. In another embodiment, the vitamin K is 1,2,3,4-tetrahydro-2-methyl-1,4-dioxo-2-naphthalenesulfonate (also known as menadione bisulfate), or a pharmaceutically acceptable solvate or hydrate thereof. Suitable bases for forming a pharmaceutically acceptable salt include, but are not limited to, inorganic bases, such as magnesium hydroxide, calcium hydroxide, potassium hydroxide, zinc hydroxide, and sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

In one embodiment, vitamin $K_3$ is an alkali or alkaline earth metal salt of 1,2,3,4-tetrahydro-2-methyl-1,4-dioxo-2-naphthalenesulfonic acid, or a pharmaceutically acceptable solvate or hydrate thereof. In another embodiment, vitamin $K_3$ is sodium, potassium, calcium, or magnesium 1,2,3,4-tetrahydro-2-methyl-1,4-dioxo-2-naphthalenesulfonate, or a pharmaceutically acceptable solvate or hydrate thereof. In yet another embodiment, vitamin $K_3$ is sodium 1,2,3,4-tetrahydro-2-methyl-1,4-dioxo-2-naphthalenesulfonate, or a pharmaceutically acceptable solvate or hydrate thereof. In yet another embodiment, vitamin $K_3$ is potassium 1,2,3,4-tetrahydro-2-methyl-1,4-dioxo-2-naphthalenesulfonate, or a pharmaceutically acceptable solvate or hydrate thereof. In yet another embodiment, vitamin $K_3$ is magnesium 1,2,3,4-tetrahydro-2-methyl-1,4-dioxo-2-naphthalenesulfonate, or a pharmaceutically acceptable solvate or hydrate thereof. In yet another embodiment, vitamin $K_3$ is sodium 1,2,3,4-tetrahydro-2-methyl-1,4-dioxo-2-naphthalenesulfonate. In yet another embodiment, vitamin $K_3$ is anhydrous sodium 1,2,3,4-tetrahydro-2-methyl-1,4-dioxo-2-naphthalenesulfonate. In yet another embodiment, vitamin $K_3$ is sodium 1,2,3,4-tetrahydro-2-methyl-1,4-dioxo-2-naphthalenesulfonate hydrate. In still another embodiment, vitamin $K_3$ is sodium 1,2,3,4-tetrahydro-2-methyl-1,4-dioxo-2-naphthalenesulfonate trihydrate.

In certain embodiments, the vitamin K is vitamin $K_4$, or a pharmaceutically acceptable salt, solvate, or hydrate thereof. Vitamin $K_4$ is also known as menadiol, 2-methyl-1,4-naphthalenediol, 2-methyl-1,4-naphthohydroquinone, 2-methyl-1,4-naphthoquinol, and dihydrovitamin $K_3$. In certain embodiments, the vitamin K is menadiol sodium diphosphate.

In certain embodiments, the vitamin K comprises vitamin $K_3$ and vitamin $K_4$, or pharmaceutically acceptable salts, solvates, or hydrates thereof.

In certain embodiments, the vitamin K is vitamin $K_5$, or a pharmaceutically acceptable salt, solvate, or hydrate thereof. Vitamin $K_5$ is also known as 4-amino-2-methyl-1-naphthalenol, 4-amino-2-methyl-1-naphthol, 1-hydroxy-2-methyl-4-aminonaphalene, 2-methyl-4-amino-1-hydroxynaphthalene, 2-methyl-4-amino-1-naphthol, 3-methyl-4-hydroxy-1-naphthylamine, and synkamin.

In certain embodiments, the vitamin K is chromium-free. In certain embodiments, the chromium-free vitamin K contains no more than 100 ppm, 50 ppm, 20 ppm, 10 ppm, 5 ppm, 2 ppm, 1 ppm, 0.1 ppm, 10 ppb, or 1 ppb of chromium. In certain embodiments, the chromium-free vitamin K contains no greater than 10 ppm of chromium. In certain embodiments, the chromium-free vitamin K contains no greater than 5 ppm of chromium. In certain embodiments, the chromium-free vitamin K contains no greater than 2 ppm of chromium. In certain embodiments, the chromium-free vitamin K contains no greater than 1 ppm of chromium.

In certain embodiments, the vitamin K is chromium-free vitamin $K_3$. In certain embodiments, the chromium-free vitamin $K_3$ contains no more than 100 ppm, 50 ppm, 20 ppm, 10 ppm, 5 ppm, 2 ppm, 1 ppm, 0.1 ppm, 10 ppb, or 1 ppb of chromium. In certain embodiments, the chromium-free vitamin $K_3$ contains no greater than 10 ppm of chromium. In certain embodiments, the chromium-free vitamin $K_3$ contains no greater than 5 ppm of chromium. In certain embodiments, the chromium-free vitamin $K_3$ contains no greater than 2 ppm of chromium. In certain embodiments, the chromium-free vitamin $K_3$ contains no greater than 1 ppm of chromium.

In certain embodiments, the vitamin K is chromium-free sodium 1,2,3,4-tetrahydro-2-methyl-1,4-dioxo-2-naphthalenesulfonate. In certain embodiments, the chromium-free sodium 1,2,3,4-tetrahydro-2-methyl-1,4-dioxo-2-naphthalenesulfonate contains no more than 100 ppm, 50 ppm, 20 ppm, 10 ppm, 5 ppm, 2 ppm, 1 ppm, 0.1 ppm, 10 ppb, or 1 ppb of chromium. In certain embodiments, the chromium-free sodium 1,2,3,4-tetrahydro-2-methyl-1,4-dioxo-2-naphthalenesulfonate contains no greater than 10 ppm of chromium. In certain embodiments, the chromium-free sodium 1,2,3,4-tetrahydro-2-methyl-1,4-dioxo-2-naphthalenesulfonate contains no greater than 5 ppm of chromium. In certain embodiments, the chromium-free sodium 1,2,3,4-tetrahydro-2-methyl-1,4-dioxo-2-naphthalenesulfonate contains no greater than 2 ppm of chromium. In certain embodiments, the chromium-free sodium 1,2,3,4-tetrahydro-2-methyl-1,4-dioxo-2-naphthalenesulfonate contains no greater than 1 ppm of chromium.

In certain embodiments, the chromium-free vitamin $K_3$ is made via a cerium mediator electrochemical technology (CETECH™) as described in U.S. Pat. No. 6,468,414, the disclosure of which is incorporated by reference herein in its entirety. Alternatively, chromium-free vitamin $K_3$ is available from commercial sources, such as PRO-K™ (Lonza Group Ltd, Switzerland).

In one embodiment, the quinone compound is one that is capable of increasing the production of a reactive oxygen species (e.g., in one embodiment superoxide anon, in another embodiment, hydrogen peroxide) in a cell.

In another embodiment, the quinone compound is one that is capable of inducing autoschizis. Taper et al., *J. Histochem. Cytochem.* 2001, 49, 109-119; Jamison et al., *Biochem. Pharm.* 2002, 63, 1773-1783; the disclosure of each of which is incorporated herein by reference in its entirety.

In certain embodiments, the quinone compound is a naphthalenedione, optionally substituted with one or more substituents Q as defined herein. In certain embodiments, the quinone compound is a naphthalene-1,2-dione, optionally substituted with one or more substituents Q as defined herein. In certain embodiments, the quinone compound is a naphthalene-1,4-dione, optionally substituted with one or more substituents Q as defined herein. In certain embodiments, the quinone compound is a naphthalene-1,4-dione, substituted with one, two, three, or four substituents Q, each of which is independently selected from amino, halo, cyano, nitro, $C_{1-6}$ alkyl, —$OR^a$, —$SR^a$, and —$COR^a$, wherein $R^a$ is (i) hydrogen; or (ii) $C_{1-6}$ alkyl, $C_{6-15}$ aryl, or heteroaryl, each optionally substituted with one or more substituents Q. In certain embodiments, the quinone compound is a naphthalene-1,4-dione, substituted with one, two, three, or four substituents Q, each of which is independently selected from amino, bromo, chloro, cyano, nitro, methyl, —$OR^a$, —$SR^a$, and —$COR^a$, wherein $R^a$ is hydrogen, methyl, phenyl, chlorophenyl, fluorophenyl, tert-butylphenyl, methoxyphenyl, trimethoxyphenyl, or (methoxy-2-oxo-2H-chromenyl)methyl. In certain embodiments, the quinone compound is a naphthalene-1,4-dione, substituted with one, two, three, or four substituents Q, each of which is independently selected from amino, bromo, chloro, cyano, nitro, methyl, —$OR^a$, —$SR^a$, and —$COR^a$, wherein $R^a$ is hydrogen, methyl, phenyl, 2-chlorophenyl, 3-chlorophenyl, 4-fluorophenyl, 4-tert-butylphenyl, 4-methoxyphenyl, 3,4,5-trimethoxyphenyl, or (7-methoxy-2-oxo-2H-chromen-4-yl)methyl. Additional quinone compounds include, but are not limited to, those disclosed in U.S. Pat. App. Pub. No. 2013/0219528; and Benites et al. *Invest. New Drugs* 2011, 29, 760-767; the disclosure of each of which is incorporated herein by reference in its entirety.

In certain embodiments, the quinone compound is 2-bromo-1,4-naphthoquinone, 2-methoxy-1,4-naphthoquinone, or 2-methyl-1,4-naphthoquinone; or a pharmaceutically acceptable salt, solvate, hydrate, or prodrug thereof. In certain embodiments, the quinone compound is 2-(((7-methoxy-2-oxo-2H-chromen-4-yl)methyl)thio)naphthalene-1,4-dione, or a pharmaceutically acceptable salt, solvate, hydrate, or prodrug thereof. Additional quinone compounds include, but are not limited to, those disclosed in Bana et al., *Mol. Carcinog.* 2015, 54, 242-247, the disclosure of which is incorporated herein by reference in its entirety; or pharmaceutically acceptable salts, solvates, hydrates, and prodrugs thereof.

In certain embodiments, the quinone compound is 2-amino-3-bromo-1,4-naphthoquinone, 2-amino-3-chloro-1,4-naphthoquinone, or 2-amino-3-methoxy-1,4-naphthoquinone; or a pharmaceutically acceptable salt, solvate, hydrate, or prodrug thereof. In certain embodiments, the quinone compound is 2,3-dichloro-1,4-naphthoquinone or 2,3-dimethoxy-1,4-naphthoquinone; or a pharmaceutically acceptable salt, solvate, hydrate, or prodrug thereof. Additional quinone compounds include, but are not limited to, those disclosed in Graciani and Ximenes, *Braz. J. Med. Biol. Res.* 2012, 45, 701-710, the disclosure of which is incorporated herein by reference in its entirety; or pharmaceutically acceptable salts, solvates, hydrates, and prodrugs thereof.

In certain embodiments, the quinone compound is 2-dibenzoylamino-3-chloro-1,4-naphthoquinone, 2-dibenzoylamino-3-bromo-1,4-naphthoquinone, 2-dibenzoylamino-3-methoxy-1,4-naphthoquinone, 2-bis-(2-chlorobenzoyl)amino-3-chloro-1,4-naphthoquinone, 2-bis-(2-chlorobenzoyl)amino-3-bromo-1,4-naphthoquinone, 2-bis-(2-chlorobenzoyl)amino-3-methoxy-1,4-naphthoquinone, 2-bis-(3-chlorobenzoyl)amino-3-chloro-1,4-naphthoquinone, 2-bis-(3-chlorobenzoyl)amino-3-bromo-1,4-naphthoquinone, 2-bis-(3-chlorobenzoyl)amino-3-methoxy-1,4-naphthoquinone, 2-bis-(4-chlorobenzoyl)amino-3-chloro-1,4-naphthoquinone, 2-bis-(4-chlorobenzoyl)amino-3-bromo-1,4-naphthoquinone, 2-bis-(4-chlorobenzoyl)amino-3-methoxy-1,4-naphthoquinone, 2-bis-(4-fluorobenzoyl)amino-3-chloro-1,4-naphthoquinone, 2-bis-(4-fluorobenzoyl)amino-3-bromo-1,4-naphthoquinone, 2-bis-(4-fluorobenzoyl)amino-3-methoxy-1,4-naphthoquinone, 2-bis-(4-tert-butylbenzoyl)amino-3-chloro-1,4-naphthoquinone, 2-bis-(4-tert-butylbenzoyl)amino-3-bromo-1,4-naphthoquinone, 2-bis-(4-tert-butylbenzoyl)amino-3-methoxy-1,4-naphthoquinone, 2-bis-(4-methoxybenzoyl)amino-3-chloro-1,4-naphthoquinone, 2-bis-(4-methoxybenzoyl)amino-3-bromo-1,4-naphthoquinone, 2-bis-(3,4,5-trimethoxybenzoyl)-amino-3-chloro-1,4-naphthoquinone, 2-N-(4-chlorobenzoyl))-amino-3-chloro-1,4-naphthoquinone, 2-(N-benzoyl-N-(4-chlorobenzoyl))-amino-3-chloro-1,4-naphthoquinone, 2-N-acteylamino-3-chloro-1,4-naphthoquinone, or 2-(N-acetyl-N-(4-chlorobenzoyl))-amino-3-chloro-1,4-naphthoquinone; or a pharmaceutically acceptable salt, solvate, hydrate, or prodrug thereof. Additional quinone compounds include, but are not limited to, those disclosed in Brandy et al., *Molecules* 2013, 18, 1973-1984, the disclosure of which is incorporated herein by reference in its entirety; or pharmaceutically acceptable salts, solvates, hydrates, and prodrugs thereof.

In certain embodiments, the quinone compound is plumbagin, also known as 5-hydroxy-2-methyl-naphthalene-1,4-dione. In certain embodiments, the quinone compound is plumbazeylanone. In certain embodiments, the quinone compound is lawsone, also known as 2-hydroxy-1,4-naphthoquinone. In certain embodiments, the quinone compound is juglone, also known as 5-hydroxy-1,4-naphthalenedione. Additional quinone compounds include, but are not limited to, those disclosed in Padhye et al., *Med. Res. Rev.* 2012, 32, 1131-1158, the disclosure of which is incorporated herein by reference in its entirety; or pharmaceutically acceptable salts, solvates, hydrates, and prodrugs thereof.

In certain embodiments, the quinone compound is mitomycin C, also known as [6-amino-8a-methoxy-5-methyl-4,7-dioxo-1,1a,2,4,7,8,8a,8b-octahydroazireno[2',3':3,4]-pyrrolo[1,2-a]indol-8-yl]methyl carbamate. In certain embodiments, the quinone compound is daunorubicin, also known as (8S,10S)-8-acetyl-10-[(2S,4S,5S,6S)-4-amino-5-hydroxy-6-methyl-oxan-2-yl]oxy-6,8,11-trihydroxy-1-methoxy-9,10-dihydro-7H-tetracene-5,12-dione. In certain embodiments, the quinone compound is doxorubicin, also known as (7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione. In certain embodiments, the quinone compound is mitoxantrone, also known as 1,4-dihydroxy-5,8-bis[2-(2-hydroxyethylamino)ethylamino]-anthracene-9,10-dione.

In certain embodiments, the quinone compound is chromium-free. In certain embodiments, the chromium-free quinone compound contains no more than 100 ppm, 50 ppm, 20 ppm, 10 ppm, 5 ppm, 2 ppm, 1 ppm, 0.1 ppm, 10 ppb, or 1 ppb of chromium. In certain embodiments, the chromium-free quinone compound contains no greater than 10 ppm of chromium. In certain embodiments, the chromium-free quinone compound contains no greater than 5 ppm of chromium. In certain embodiments, the chromium-free quinone compound contains no greater than 2 ppm of chromium. In certain embodiments, the chromium-free quinone compound contains no greater than 1 ppm of chromium.

The quinone compound may also be provided as a prodrug, which is a functional derivative of the quinone compound and is readily convertible into the parent quinone compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, Progress in Drug Research 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnej ad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Antiparasitic Agents

In one embodiment, the antiparasitic agent is an antiprotozoal, an antihelminthic, an antinematode, an anticestode, an antitrematode, an antiamoebic, or an antifungal. In another embodiment, the antiparasitic agent is albendazole, amphotericin B, benznidazole, bephenium, diethylcarbamzine, eflornithine, flubendazole, ivermectin, mebendazole, meglumine antimonite, melarsoprol, metronidazole, miltefosine, niclosamide, nifurtimox, nitazoxanide, pentavalent antimony, praziquantel, pyrantel, pyrvinium, sodium stibogluconate, thiabendazole, or tinidazole. In yet another embodiment, the antiparasitic agent is nifurtimox.

In one embodiment, the antiparasitic agent is a nitroimidazole. In another embodiment, the antiparasitic agent is a 2-nitroimidazole. In yet another embodiment, the antiparasitic agent is a 5-nitroimidazole. In yet another embodiment, the antiparasitic agent is azanidazole, dimetridazole, megazol, metronidazole, nimorazole, ornidazole, pretomanid, or tinidazole. In still another embodiment, the antiparasitic agent is benznidazole.

Pharmaceutical Compositions

In one embodiment, a pharmaceutical composition comprises (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof; or a pharmaceutically acceptable salt, solvate, hydrate, or prodrug thereof.

In certain embodiments, the pharmaceutical composition further comprises a pharmaceutically acceptable vehicle, carrier, diluent, or excipient, or a mixture of two or more thereof.

In certain embodiments, the ascorbic acid used in each of the pharmaceutical compositions is independently chromium-free. In certain embodiments, the quinone compound used in each of the pharmaceutical compositions is independently chromium-free.

In certain embodiments, the pharmaceutical compositions are each independently chromium-free. In certain embodiments, the pharmaceutical compositions each independently contain no more than 100 ppm, 50 ppm, 20 ppm, 10 ppm, 5 ppm, 2 ppm, 1 ppm, 0.1 ppm, 10 ppb, or 1 ppb of chromium. In certain embodiments, the pharmaceutical compositions each independently contain no greater than 10 ppm of chromium. In certain embodiments, the pharmaceutical compositions each independently contain no greater than 5 ppm of chromium. In certain embodiments, the pharmaceutical compositions each independently contain no greater than 2 ppm of chromium. In certain embodiments, the pharmaceutical compositions each independently contain no greater than 1 ppm of chromium.

In one embodiment, the weight ratio of the ascorbic acid to the quinone compound in each of the pharmaceutical compositions is independently ranging from about 4 to about 500, from about 10 to about 500, from about 50 to about 500, from about 25 to about 250, from about 50 to about 200, from about 50 to about 150, or from about 80 to about 120. In another embodiment, the weight ratio of the ascorbic acid to the quinone compound in each of the pharmaceutical compositions is independently about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, or about 250. In yet another embodiment, the weight ratio of the ascorbic acid to the quinone compound in each of the pharmaceutical compositions is independently about 100. In still another embodiment, the weight ratio of the ascorbic acid to the quinone compound in each of the pharmaceutical compositions is independently about 200.

In one embodiment, the molar ratio of the ascorbic acid to the quinone compound in each of the pharmaceutical compositions is independently ranging from about 10 to about 500, from about 25 to about 250, from about 50 to about 200, from about 50 to about 150, or from about 80 to about 120. In another embodiment, the molar ratio of the ascorbic acid to the quinone compound in each of the pharmaceutical compositions is independently about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, or about 250. In yet another embodiment, the molar ratio of the ascorbic acid to the quinone compound in each of the pharmaceutical compositions is independently about 100. In still another embodiment, the molar ratio of the ascorbic acid to the quinone compound in each of the pharmaceutical compositions is independently about 200.

In certain embodiments, the pharmaceutical compositions are each independently formulated in various dosage forms for oral, parenteral, and topical administration. In certain embodiments, the pharmaceutical compositions are each independently formulated as modified release dosage forms, including, but not limited to, delayed-, extended-, prolonged-, sustained-, pulsatile-, controlled-, accelerated-, fast-, targeted-, and programmed-release; and gastric retention dosage forms. These dosage forms can be prepared according to conventional methods and techniques known to those skilled in the art (See, e.g., *Remington: The Science and Practice of Pharmacy, supra; Modified-Release Drug Delivery Technology*, Rathbone et al., Eds., Drugs and the Pharmaceutical Sciences, CRC Press LLC: 2008; Vol. 183).

In one embodiment, the pharmaceutical compositions are each independently formulated in a dosage form for oral administration. In another embodiment, the pharmaceutical compositions are each independently formulated in a dosage form for parenteral administration. In yet another embodiment, the pharmaceutical compositions are each independently formulated in a dosage form for intravenous administration. In yet another embodiment, the pharmaceutical compositions are each independently formulated in a dosage form for topical administration. In still another embodiment, the pharmaceutical compositions are each independently formulated in a dosage form for local injection.

In one embodiment, the pharmaceutical compositions are each independently formulated as a capsule. In one embodiment, the capsule comprises (i) from about 10 mg to about 1,000 mg, from about 25 mg to about 900 mg, from about 50 mg to about 800 mg, from about 100 mg to about 700 mg, from about 200 mg to about 600 mg, from about 300 mg to about 600 mg, or from about 400 mg to about 600 mg of ascorbic acid, or a single enantiomer, a mixture of enantiomers, or a mixture of diastereomers thereof; or a pharmaceutically acceptable salt, solvate, or hydrate thereof; and (ii) from about 0.1 mg to about 10 mg, from about 1 mg to about 9 mg, from about 2 mg to about 8 mg, from about 3 mg to about 7 mg, or from about 4 mg to about 6 mg of a quinone compound, or a single enantiomer, a mixture of enantiomers, or a mixture of diastereomers thereof, or a pharmaceutically acceptable salt, solvate, hydrate, or prodrug thereof.

In another embodiment, the capsule comprises (i) from about 400 mg to about 600 mg of ascorbic acid, or a single enantiomer, a mixture of enantiomers, or a mixture of diastereomers thereof; or a pharmaceutically acceptable salt, solvate, or hydrate thereof; and (ii) from about 4 mg to about 6 mg of a quinone compound, or a single enantiomer, a mixture of enantiomers, or a mixture of diastereomers thereof, or a pharmaceutically acceptable salt, solvate, hydrate, or prodrug thereof.

In yet another embodiment, the capsule comprises (i) about 200 mg, about 300 mg, about 400, about 500, about 600 mg, about 700 mg, about 800 mg, or about 900 mg of ascorbic acid, or a single enantiomer, a mixture of enantiomers, or a mixture of diastereomers thereof; or a pharmaceutically acceptable salt, solvate, or hydrate thereof; and (ii) about 1 mg, about 2 mg, about 3 mg, about 4 mg, about 5 mg, about 6 mg, about 7 mg, about 8 mg, about 9 mg, or about 10 mg of a quinone compound, or a single enantiomer, a mixture of enantiomers, or a mixture of diastereomers thereof, or a pharmaceutically acceptable salt, solvate, hydrate, or prodrug thereof.

In still another embodiment, the capsule comprises (i) about 500 mg of ascorbic acid, or a single enantiomer, a mixture of enantiomers, or a mixture of diastereomers thereof; or a pharmaceutically acceptable salt, solvate, or hydrate thereof; and (ii) about 5 mg of a quinone compound, or a single enantiomer, a mixture of enantiomers, or a mixture of diastereomers thereof, or a pharmaceutically acceptable salt, solvate, hydrate, or prodrug thereof.

In certain embodiments, the capsule consists essentially of (i) ascorbic acid, or a single enantiomer, a mixture of enantiomers, or a mixture of diastereomers thereof or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof.

In certain embodiments, the capsule contains (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof.

In one embodiment, the ascorbic acid compound in each of the pharmaceutical compositions is independently L-ascorbic acid or a pharmaceutically acceptable salt thereof, or a pharmaceutically acceptable solvate or hydrate thereof. In another embodiment, the ascorbic acid compound in each of the pharmaceutical compositions is independently an alkali or alkaline earth metal salt of L-ascorbic acid, or a pharmaceutically acceptable solvate or hydrate thereof; or a mixture thereof. In yet another embodiment, the ascorbic acid compound in each of the pharmaceutical compositions is independently sodium, potassium, calcium, or magnesium salt of L-ascorbic acid, or a pharmaceutically acceptable solvate or hydrate thereof; or a mixture thereof. In yet another embodiment, the ascorbic acid compound in each of the pharmaceutical compositions is independently sodium L-ascorbate. In yet another embodiment, the ascorbic acid compound in each of the pharmaceutical compositions is independently calcium L-ascorbate. In yet another embodiment, the ascorbic acid compound in each of the pharmaceutical compositions is independently magnesium L-ascorbate. In still another embodiment, the ascorbic acid compound in each of the pharmaceutical compositions is independently a mixture of two or three of sodium L-ascorbate, calcium L-ascorbate, and magnesium L-ascorbate.

In one embodiment, the quinone compound in each of the pharmaceutical compositions is independently vitamin K, or a single enantiomer, a mixture of enantiomers, or a mixture of diastereomers thereof, or a pharmaceutically acceptable salt, solvate, or hydrate thereof. In another embodiment, the quinone compound in each of the pharmaceutical compositions is independently vitamin $K_3$, or a pharmaceutically acceptable salt, solvate, or hydrate thereof. In yet another embodiment, the quinone compound in each of the pharmaceutical compositions is independently 2-methyl-1,4-naphthalenedione, or a pharmaceutically solvate or hydrate thereof. In yet another embodiment, the quinone compound in each of the pharmaceutical compositions is independently 2-methyl-1,4-naphthalenedione. In yet another embodiment, the quinone compound in each of the pharmaceutical compositions is independently 1,2,3,4-tetrahydro-2-methyl-1,4-dioxo-2-naphthalenesulfonic acid, or a pharmaceutically acceptable salt, solvate, or hydrate thereof. In yet another embodiment, the quinone compound in each of the pharmaceutical compositions is independently an alkali or alkaline earth metal salt of 1,2,3,4-tetrahydro-2-methyl-1,4-dioxo-2-naphthalenesulfonic acid, or a pharmaceutically acceptable solvate or hydrate thereof; or a mixture thereof. In yet another embodiment, the quinone compound in each of the pharmaceutical compositions is independently sodium, potassium, calcium, or magnesium 1,2,3,4-tetrahydro-2-methyl-1,4-dioxo-2-naphthalenesulfonate, or a pharmaceutically acceptable solvate or hydrate thereof; or a mixture thereof. In yet another embodiment, the quinone compound in each of the pharmaceutical compositions is independently sodium 1,2,3,4-tetrahydro-2-methyl-1,4-dioxo-2-naphthalenesulfonate, or a pharmaceutically acceptable solvate or hydrate thereof. In yet another embodiment, the quinone compound in each of the pharmaceutical compositions is independently potassium 1,2,3,4-tetrahydro-2-methyl-1,4-dioxo-2-naphthalenesulfonate, or a pharmaceutically acceptable solvate or hydrate thereof. In yet another embodiment, the quinone compound in each of the pharmaceutical compositions is independently magnesium 1,2,3,4-tetrahydro-2-methyl-1,4-dioxo-2-naphthalenesulfonate, or a pharmaceutically acceptable solvate or hydrate thereof. In yet another embodiment, the quinone compound in each of the pharmaceutical compositions is independently sodium 1,2,3,4-tetrahydro-2-methyl-1,4-dioxo-2-naphthalenesulfonate. In yet another embodiment, the quinone compound in each of the pharmaceutical compositions is independently anhydrous sodium 1,2,3,4-tetrahydro-2-methyl-1,4-dioxo-2-naphthalenesulfonate. In yet another embodiment, the quinone compound in each of the pharmaceutical compositions is independently sodium 1,2,3,4-tetrahydro-2-methyl-1,4-dioxo-2-naphthalenesulfonate hydrate. In still another embodiment, the quinone compound in each of the pharmaceutical compositions is independently sodium 1,2,3,4-tetrahydro-2-methyl-1,4-dioxo-2-naphthalenesulfonate trihydrate.

In one embodiment, the capsule contains about 500 mg of sodium L-ascorbate, and about 5 mg of sodium 1,2,3,4-tetrahydro-2-methyl-1,4-dioxo-2-naphthalenesulfonate or a hydrate thereof. In another embodiment, the capsule contains about 500 mg of calcium L-ascorbate, and about 5 mg of sodium 1,2,3,4-tetrahydro-2-methyl-1,4-dioxo-2-naphthalenesulfonate or a hydrate thereof. In yet another embodiment, the capsule contains about 500 mg of magnesium L-ascorbate, and about 5 mg of sodium 1,2,3,4-tetrahydro-2-methyl-1,4-dioxo-2-naphthalenesulfonate or hydrate thereof. In yet another embodiment, the capsule contains about 500 mg of sodium L-ascorbate and about 5 mg of anhydrous sodium 1,2,3,4-tetrahydro-2-methyl-1,4-dioxo-2-naphthalenesulfonate. In yet another embodiment, the capsule contains about 500 mg of sodium L-ascorbate and about 5 mg of sodium 1,2,3,4-tetrahydro-2-methyl-1,4-dioxo-2-naphthalenesulfonate trihydrate. In yet another embodiment, the capsule contains about 500 mg of calcium L-ascorbate and about 5 mg of anhydrous sodium 1,2,3,4-tetrahydro-2-methyl-1,4-dioxo-2-naphthalenesulfonate. In yet another embodiment, the capsule contains about 500 mg of calcium L-ascorbate and about 5 mg of sodium 1,2,3,4-tetrahydro-2-methyl-1,4-dioxo-2-naphthalenesulfonate trihydrate. In yet another embodiment, the capsule contains about 500 mg of magnesium L-ascorbate and about 5 mg of anhydrous sodium 1,2,3,4-tetrahydro-2-methyl-1,4-dioxo-2-naphthalenesulfonate. In still another embodiment, the capsule contains about 500 mg of magnesium L-ascorbate and about 5 mg of sodium 1,2,3,4-tetrahydro-2-methyl-1,4-dioxo-2-naphthalenesulfonate trihydrate. In another embodiment, the capsule further comprises a pharmaceutically acceptable vehicle, carrier, diluent, or excipient, or a mixture of two or more thereof.

In one embodiment, the capsule contains about 500 mg of sodium L-ascorbate and about 5 mg of 2-methyl-1,4-naphthalenedione. In another embodiment, the capsule contains about 1,000 mg of sodium L-ascorbate and about 10 mg of 2-methyl-1,4-naphthalenedione. In yet another embodiment, the capsule contains about 925 mg of sodium L-ascorbate and about 9 mg (e.g., 9.25 mg) of 2-methyl-1,4-naphthalenedione.

In one embodiment, the capsule contains about 500 mg of calcium L-ascorbate and about 5 mg of 2-methyl-1,4-naphthalenedione. In another embodiment, the capsule contains about 1,000 mg of calcium L-ascorbate and about 10 mg of 2-methyl-1,4-naphthalenedione. In yet another embodiment, the capsule contains about 925 mg of calcium L-ascorbate and about 9 mg (e.g., 9.25 mg) of 2-methyl-1,4-naphthalenedione.

In one embodiment, the capsule contains about 500 mg of magnesium L-ascorbate and about 5 mg of 2-methyl-1,4-naphthalenedione. In another embodiment, the capsule contains about 1,000 mg of magnesium L-ascorbate and about 10 mg of 2-methyl-1,4-naphthalenedione. In yet another embodiment, the capsule contains about 925 mg of magnesium L-ascorbate and about 9 mg (e.g., 9.25 mg) of 2-methyl-1,4-naphthalenedione.

In one embodiment, the capsule consists essentially of ascorbic acid, or a single enantiomer, a mixture of enantiomers, or a mixture of diastereomers thereof; or a pharmaceutically acceptable salt, solvate, or hydrate thereof; and vitamin K, or a single enantiomer, a mixture of enantiomers, or a mixture of diastereomers thereof, or a pharmaceutically acceptable salt, solvate, or hydrate thereof. In another embodiment, the capsule consists essentially of ascorbic acid, or a single enantiomer, a mixture of enantiomers, or a mixture of diastereomers thereof; or a pharmaceutically acceptable salt, solvate, or hydrate thereof; and vitamin $K_3$, or a pharmaceutically acceptable salt, solvate, or hydrate thereof.

In one embodiment, the capsule consists essentially of sodium L-ascorbate and 2-methyl-1,4-naphthalenedione. In another embodiment, the capsule consists essentially of calcium L-ascorbate and 2-methyl-1,4-naphthalenedione. In yet another embodiment, the capsule consists essentially of magnesium L-ascorbate and 2-methyl-1,4-naphthalenedione.

In one embodiment, the capsule consists essentially of sodium L-ascorbate, and sodium 1,2,3,4-tetrahydro-2-methyl-1,4-dioxo-2-naphthalenesulfonate or a hydrate thereof. In another embodiment, the capsule consists essentially of calcium L-ascorbate, and sodium 1,2,3,4-tetrahydro-2-methyl-1,4-dioxo-2-naphthalenesulfonate or hydrate thereof. In yet another embodiment, the capsule consists essentially of magnesium L-ascorbate, and sodium 1,2,3,4-tetrahydro-2-methyl-1,4-dioxo-2-naphthalenesulfonate or hydrate thereof.

In one embodiment, the capsule consists essentially of sodium L-ascorbate and anhydrous sodium 1,2,3,4-tetrahydro-2-methyl-1,4-dioxo-2-naphthalenesulfonate. In another embodiment, the capsule consists essentially of sodium L-ascorbate and sodium 1,2,3,4-tetrahydro-2-methyl-1,4-dioxo-2-naphthalenesulfonate trihydrate. In yet another embodiment, the capsule consists essentially of calcium L-ascorbate and anhydrous sodium 1,2,3,4-tetrahydro-2-methyl-1,4-dioxo-2-naphthalenesulfonate. In yet another embodiment, the capsule consists essentially of calcium L-ascorbate and sodium 1,2,3,4-tetrahydro-2-methyl-1,4-dioxo-2-naphthalenesulfonate trihydrate. In yet another embodiment, the capsule consists essentially of magnesium L-ascorbate and anhydrous sodium 1,2,3,4-tetrahydro-2-methyl-1,4-dioxo-2-naphthalenesulfonate. In still another embodiment, the capsule consists essentially of magnesium L-ascorbate and sodium 1,2,3,4-tetrahydro-2-methyl-1,4-dioxo-2-naphthalenesulfonate trihydrate.

The pharmaceutical compositions can also be formulated as known to those skilled in the art. Some examples of pharmaceutical compositions that contain an ascorbic acid compound and a quinone compound are described in U.S. Pat. Nos. 7,091,241 and 8,507,555; and U.S. Pat. App. Pub. Nos. US 2012/184609, US 2013/178522, and US 2014/0200270; each of which is incorporated herein by reference in its entirety.

In certain embodiments, the pharmaceutical compositions are each independently provided in a unit-dosage or multiple-dosage form. A unit-dosage form, as used herein, refers to a physically discrete unit suitable for administration to a subject, e.g., a human and animal subject, and packaged individually as is known in the art. Each unit-dose contains a predetermined quantity of one or more active ingredient(s) sufficient to produce the desired therapeutic effect, optionally in association with one or more pharmaceutical vehicle(s), carrier(s), diluent(s), or excipient(s). Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

B. Oral Administration

The pharmaceutical compositions for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gums, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carrier(s) or excipient(s), including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginate, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), and hydroxypropyl methyl cellulose (HPMC); microcrystalline celluloses, such as AVICEL-PH-101, AVICEL-PH-103, AVICEL RC-581, and AVICEL-PH-105 (FMC Corp., Marcus Hook, PA); pectin; and mixtures of two or more thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures of two or more thereof. The amount of a binder or filler in the pharmaceutical compositions varies upon the type of formulation, and is readily discernible to those of ordinary skill in the art. The binder or filler may be present from about 50% to about 99% by weight in the pharmaceutical compositions.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions varies depending on the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; algins; pectin; and mixtures of two or more thereof. The amount of a disintegrant in the pharmaceutical compositions varies upon the type of formulation, and is readily discernible to those of ordinary skill in the art. The pharmaceutical compositions may contain from about 0.5% to about 15% or from about 1% to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, MD) and CAB-O-SIL® (Cabot Co. of Boston, MA); and mixtures of two or more thereof. The pharmaceutical compositions may contain from about 0.1% to about 5% by weight of a lubricant.

Suitable glidants include, but are not limited to, colloidal silicon dioxide, CAB-O-SIL® (Cabot Co. of Boston, MA), and asbestos-free talc. Suitable coloring agents include, but are not limited to, any of the approved, certified, water soluble FD&C dyes, and water insoluble FD&C dyes suspended on alumina hydrate, and color lakes and mixtures of two or more thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic acid, sodium benzoate, and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions for oral administration can be provided as compressed tablets, tablet triturates, chewable lozenges, rapidly dissolving tablets, multiple compressed tablets, enteric-coated tablets, or sugar-coated or film-coated tablets. In one embodiment, enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of, e.g., a water-soluble material. Film coatings include, but are not limited to, hydroxyethylcellulose, sodium carboxymethylcellulose, polyethylene glycol 4000, and cellulose acetate phthalate. In one embodiment, film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carrier(s) or excipient(s) described herein, including binders, disintegrants, controlled-release polymers, lubricants, diluents, and/or colorants. Flavoring and sweetening agents are useful in the formation of chewable tablets and lozenges.

The pharmaceutical compositions for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including, but not limited to, methyl- and propylparabens, and sorbic acid. The liquid, semisolid, and solid dosage forms may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545, each of which is incorporated by reference herein in their entireties. The capsules may also be coated as known by those of skill in the art in order to modify or sustain dissolution of the active ingredient.

The pharmaceutical compositions for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions for oral administration can also be provided in the forms of liposomes, micelles, microspheres, or nanosystems. Micellar dosage forms can be prepared as described in U.S. Pat. No. 6,350,458, which is incorporated herein by reference in its entirety.

The pharmaceutical compositions for oral administration can be provided as non-effervescent or effervescent, granules or powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions for oral administration can be formulated as immediate- or modified-release dosage forms, including delayed-, sustained-, pulsed-, controlled-, targeted-, and programmed-release forms.

C. Parenteral Administration

The pharmaceutical compositions can be administered parenterally by injection, infusion, or implantation, for local or systemic administration. Parenteral administration, as used herein, includes intravenous, intraarterial, intraperitoneal, intrathecal, intraventricular, intraurethral, intrasternal, intracranial, intramuscular, intrasynovial, intravesical, and subcutaneous administration.

The pharmaceutical compositions for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., Remington: The Science and Practice of Pharmacy, supra).

The pharmaceutical compositions intended for parenteral administration can include one or more pharmaceutically acceptable carrier(s) and excipient(s), including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringer's injection, isotonic dextrose injection, sterile water injection, dextrose and lactated Ringer's injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including, but not limited to, sodium carboxymethylcelluose, hydroxypropyl methylcellulose, and polyvinylpyrrolidone. Suitable emulsifying agents are those described herein, including, but not limited to, polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutyle-ther-β-cyclodextrin, and sulfobutylether 7-β-cyclodextrin (CAPTISOL®, CyDex, Lenexa, KS).

When the pharmaceutical compositions are formulated for multiple dosage administration, the multiple dosage parenteral formulations contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including, e.g., lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions for parenteral administration can be formulated as immediate- or modified-release dosage forms, including, e.g., delayed-, sustained-, pulsed-, controlled-, targeted-, and programmed-release forms.

The pharmaceutical compositions for parenteral administration can be formulated as a suspension, solid, semi-solid, or thixotropic liquid, for administration as an implanted depot. In one embodiment, the pharmaceutical compositions are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include, but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, and ethylene/vinyloxyethanol copolymer.

D. Topical Administration

The pharmaceutical compositions can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions can be formulated in any dosage forms that are suitable for topical administration for local or systemic effect, including, e.g., emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions can also comprise liposomes, micelles, microspheres, nanosystems, and mixtures of two or more thereof.

Pharmaceutically acceptable carriers and excipients suitable for use in the topical formulations include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, CA), and BIOJECT™ (Bioject Medical Technologies Inc., Tualatin, OR).

The pharmaceutical compositions can be provided in the forms of ointments, creams, and gels. Suitable ointment vehicles include, e.g., oleaginous or hydrocarbon vehicles, including lard, benzoinated lard, olive oil, cottonseed oil, and other oils; white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; and emulsion vehicles, either water-in-oil (W/O) emulsions or oil-in-water (O/W) emulsions, including cetyl alcohol, glyceryl monostearate, lanolin, and stearic acid (see, e.g., Remington: The Science and Practice of Pharmacy, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in, e.g., *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions; and antioxidants as described herein, including, e.g., bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, appropriate mixtures of mono-, di- and tri-glycerides of fatty acids, and hydrogels, such as polyvinyl alcohol, hydroxy-ethyl methacrylate, and polyacrylic acid. Combinations of the various vehicles can also be used. Rectal and vaginal suppositories may be prepared by compressing or molding. The typical weight of a rectal and vaginal suppository is about 2 g to about 3 g.

The pharmaceutical compositions can be administered ophthalmically in the forms of solutions, suspensions, ointments, emulsions, gel-forming solutions, powders for solutions, gels, ocular inserts, and implants.

The pharmaceutical compositions can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including, e.g., chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient(s) provided herein; a propellant as solvent; and/or a surfactant, such as sorbitan trioleate, oleic acid, or an oligolactic acid.

The pharmaceutical compositions can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions; a suitable powder base, such as lactose or starch; and a performance modifier, such as L-leucine, mannitol, or magnesium stearate. The lactose may be anhydrous or in the form of a monohydrate. Other suitable excipients or carriers include, but are not limited to, dextran, glucose, maltose, sorbitol, xylitol, fructose, sucrose, and trehalose. The pharmaceutical compositions for inhaled/intranasal administration can further comprise a suitable flavor, such as menthol and/or levomenthol; and/or sweeteners, such as saccharin and/or saccharin sodium.

The pharmaceutical compositions for topical administration can be formulated to be immediate-release or modified-release, including delayed-, sustained-, pulsed-, controlled-, targeted-, and programmed-release.

E. Modified Release

The pharmaceutical compositions can be formulated as a modified release dosage form. As used herein, the term "modified release" refers to a dosage form in which the rate or place of release of the active ingredient(s) is different from that of an immediate-release dosage form when administered by the same route. Modified release dosage forms include, but are not limited to, delayed-, extended-, prolonged-, sustained-, pulsatile-, controlled-, accelerated- or fast-, targeted-, and programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and/or polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; the contents of which are incorporated by reference herein in their entireties.

1. Matrix Controlled Release Devices

The pharmaceutical compositions in a modified release dosage form can be fabricated using a matrix controlled release device known to those skilled in the art (see, e.g., Takada et al. in "Encyclopedia of *Controlled Drug* Delivery," Vol. 2, Mathiowitz Ed., Wiley, 1999).

In certain embodiments, the pharmaceutical compositions in a modified release dosage form are formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (RPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, NJ); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions in a modified release dosage form can be prepared by methods known to those skilled in the art, including direct compression, dry or wet granulation followed by compression, and melt-granulation followed by compression.

2. Osmotic Controlled Release Devices

The pharmaceutical compositions in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (RPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures of two or more thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, DE) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119, incorporated by reference herein. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220, each of which is incorporated herein by reference.

The total amount of the active ingredient(s) released and the release rate can substantially be modulated via the thickness and porosity of the semipermeable membrane, the composition of the core, and the number, size, and position of the delivery ports.

The pharmaceutical compositions in an osmotic controlled-release dosage form can further comprise additional conventional excipient(s) or carrier(s) as described herein to promote performance or processing of the formulation.

The osmotic controlled-release dosage forms can be prepared according to conventional methods and techniques known to those skilled in the art (see, e.g., Remington: The Science and Practice of Pharmacy, supra; Santus and Baker, J. Controlled Release 1995, 35, 1-21; Verma et al., Drug Development and Industrial Pharmacy 2000, 26, 695-708; Verma et al., J. Controlled Release 2002, 79, 7-27).

In certain embodiments, the pharmaceutical compositions are formulated as AMT controlled-release dosage form, which comprises an asymmetric osmotic membrane that coats a core comprising the active ingredient(s) and other pharmaceutically acceptable excipient(s) or carrier(s). See, e.g., U.S. Pat. No. 5,612,059 and WO 2002/17918, each of which is incorporated herein by reference. The AMT controlled-release dosage forms can be prepared according to conventional methods and techniques known to those skilled in the art, including, e.g., direct compression, dry granulation, wet granulation, and a dip-coating method.

In certain embodiments, the pharmaceutical compositions are formulated as ESC controlled-release dosage form, which comprises an osmotic membrane that coats a core comprising the active ingredient(s), a hydroxyethyl cellulose, and other pharmaceutically acceptable excipient(s) or carrier(s).

3. Multiparticulate Controlled Release Devices

The pharmaceutical compositions in a modified release dosage form can be fabricated as a multiparticulate controlled release device, which comprises a multiplicity of particles, granules, or pellets, ranging from about 10 μm to about 3 mm, from about 50 μm to about 2.5 mm, or from about 100 μm to about 1 mm in diameter. Such multiparticulates can be made by the processes known to those skilled in the art, including, e.g., wet- and dry-granulation, extrusion/spheronization, roller-compaction, and melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions can also be formulated to be targeted to a particular tissue, receptor, or other area of the body of the subject to be treated, including, e.g., liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307;

5,972,366; 5,900,252; 5,840,674; 5,759,542; and 5,709,874, the contents of which are incorporated by reference herein.

Methods of Use

In one embodiment, provided herein is a method of treating, preventing, or alleviating one or more symptoms of a parasitic disease in a subject, comprising administering to the subject: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

In certain embodiments, the one of more symptoms of the parasitic disease include, but are not limited to, abdominal pain, body aches, congestive heart failure, constipation due to enlarged colon, diarrhea, difficulty swallowing due to enlarged esophagus, enlargement of liver of spleen, eyelid swelling, fatigue, fever, headache, irregular heartbeat, loss of appetite, nausea, rash, sudden cardiac arrest, swollen glands, and vomiting.

In certain embodiments, the parasitic disease is African trypanosomiasis, amoebiasis, ascariasis, babesiosis, *Chagas disease*, cryptosporidiosis, cutaneous larva migrans, dirofilariasis, echinococcosis, fasciolosis, filariasis, lymphatic filariasis, giardiasis, helminthiasis, hookworm infection, leishmaniasis, visceral leishmaniasis, malaria, neurocysticercosis, onchocerciasis, protozoan infection, schistosomiasis, taeniasis, tapeworm infection, toxocariasis, toxoplasmosis, trichinosis, or zoonosis.

In certain embodiments, the parasitic disease is a protozoan infection. In certain embodiments, the parasitic disease is African sleeping sickness, amoebiasis, babesiosis, *Chagas disease*, giardiasis, leishmaniasis, malaria, or toxoplasmosis. In certain embodiments, the parasitic disease is *Chagas disease*. In certain embodiments, the parasitic disease is leishmaniasis. In certain embodiments, the parasitic disease is cutaneous leishmaniasis, mucocutaneous leishmaniasis, or visceral leishmaniasis.

In one embodiment, provided herein is a method of treating, preventing, or alleviating one or more symptoms of *Chagas disease* in a subject, comprising administering to the subject: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

In another embodiment, provided herein is a method of treating, preventing, or alleviating one or more symptoms of leishmaniasis in a subject, comprising administering to the subject: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

In another embodiment, provided herein is a method of inhibiting parasitic growth in a subject infected with a parasite, comprising administering to the subject: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

In yet another embodiment, provided herein is a method of eliminating a parasite from a subject, comprising administering to the subject: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

In yet another embodiment, provided herein is a method of increasing the quality of life of a subject infected with a parasite, comprising administering to the subject: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

In yet another embodiment, provided herein is a method of increasing the efficacy of an antiparasitic agent in a subject infected with a parasite, comprising administering to the subject a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof.

In yet another embodiment, provided herein is a method of increasing tolerance to an antiparasitic agent in a subject infected with a parasite, comprising administering to the subject a therapeutically effective amount of: (i) vitamin C, or a pharmaceutically acceptable salt, solvate, or hydrate thereof; and (ii) a vitamin K compound, or a single enantiomer, a mixture of enantiomers, or a mixture of diastereomers thereof, or a pharmaceutically acceptable salt, solvate, hydrate, or prodrug thereof.

In yet another embodiment, provided herein is a method of reducing, minimizing, or eliminating a side effect of an antiparasitic agent to a subject infected with a parasite, comprising administering to the subject a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof.

In certain embodiments, the side effect to be reduced, minimized, or eliminated includes, but is not limited to, abdominal pain, allergic dermatitis, amnesia, anemia, anorexia, anxiety, bone marrow suppression, chills, confusion, decreased appetite, depression, dermatitis, dizziness, dysgeusia, eosinophilia, fever, headache, impotence, insomnia, leukopenia, lymphadenopathy, muscle weakness, nausea, neutropenia, numbness of hands or feet, paresthesia, peripheral neuropathy, pruritus, purpura, rash, seizures, sore throat, thrombocytopenia, tremors, urticaria, vomiting, and weight loss. In certain embodiments, the side effect to be reduced, minimized, or eliminated includes, but is not limited to, amnesia, anorexia, dizziness, headache, nausea, weight loss, and vomiting. In certain embodiments, the side effect to be reduced, minimized, or eliminated includes, but is not limited to, allergic dermatitis, anorexia, bone marrow suppression, dermatitis, dysgeusia, insomnia, nausea, peripheral neuropathy, weight loss, and vomiting. In certain embodiments, the side effect to be reduced, minimized, or eliminated includes, but is not limited to, allergic dermatitis or peripheral neuropathy. In certain embodiments, the side effect to be reduced, minimized, or eliminated includes, but is not limited to, abdominal pain, anemia, decreased appetite, eosinophilia, fever, headache, leukopenia, lymphadenopathy, nausea, neutropenia, paresthesia, pruritus, purpura, rash, thrombocytopenia, urticaria, vomiting, and weight loss. In certain embodiments, the side effect to be reduced, minimized, or eliminated includes, but is not limited to, abdominal pain, decreased appetite, eosinophilia, headache, nausea, neutropenia, pruritus, rash, urticaria, vomiting, and weight loss. In certain embodiments, the side effect to be reduced, minimized, or eliminated includes, but is not limited to, hypersensitivity skin reactions.

In certain embodiments, the side effect to be reduced, minimized, or eliminated includes, but is not limited to, a side effect of benznidazole. In certain embodiments, the side effect to be reduced, minimized, or eliminated includes, but is not limited to, a side effect of nifurtimox.

In still another embodiment, provided herein is a method of reducing a toxicity of an antiparasitic agent to a subject infected with a parasite, comprising administering to the subject a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof.

In certain embodiments, the toxicity is neurotoxicity. In certain embodiments, the toxicity is bone marrow toxicity. In certain embodiments, the toxicity is nephrotoxicity. In certain embodiments, the toxicity is CNS toxicity. In certain embodiments, the toxicity is peripheral toxicity. In certain embodiments, the toxicity is gastrointestinal toxicity. In certain embodiments, the toxicity is pulmonary toxicity. In certain embodiments, the toxicity is cardiotoxicity. In certain embodiments, the toxicity is hepatotoxicity. In certain embodiments, the toxicity is metabolic toxicity. In certain embodiments, the toxicity is renal toxicity. In certain embodiments, the toxicity is dermatologic toxicity. In certain embodiments, the toxicity is immunologic toxicity. In certain embodiments, the toxicity is lung toxicity. In certain embodiments, the toxicity is genotoxicity. In certain embodiments, the toxicity is carcinogenicity. In certain embodiments, the toxicity is embryo-fetal toxicity.

In certain embodiments, the parasite is *Plasmodium, Trypanosoma, Entamoeba, Giardia, Leishmania, Toxoplasma,* or *Schistosoma*. In certain embodiments, the parasite is *Plasmodium*. In certain embodiments, the parasite is *Trypanosoma*. In certain embodiments, the parasite is *Entamoeba*. In certain embodiments, the parasite is Giardia. In certain embodiments, the parasite is *Leishmania*. In certain embodiments, the parasite is *Toxoplasma*. In certain embodiments, the parasite is *Schistosoma*. In certain embodiments, the parasite is *Entamoeba histolytica, Giardia lamblia, Leishmania aethiopica, Leishmania amazonensis, Leishmania braziliensis, Leishmania donovani, Leishmania mexicana, Leishmania major, Leishmania tropica, Plasmodium berghei, Plasmodium falciparum, Plasmodium yoelii, Schistosoma mansonii, Trypanosoma brucei, Trypanosoma cruzi,* or *Toxoplasma gondii*. In certain embodiments, the parasite is *Entamoeba histolytica*. In certain embodiments, the parasite is *Giardia lamblia*. In certain embodiments, the parasite is *Leishmania aethiopica*. In certain embodiments, the parasite is *Leishmania amazonensis*. In certain embodiments, the parasite is *Leishmania braziliensis*. In certain embodiments, the parasite is *Leishmania donovani*. In certain embodiments, the parasite is *Leishmania Mexicana*. In certain embodiments, the parasite is *Leishmania major*. In certain embodiments, the parasite is *Leishmania tropica*. In certain embodiments, the parasite is *Plasmodium berghei*. In certain embodiments, the parasite is *Plasmodium falciparum*. In certain embodiments, the parasite is *Plasmodium yoelii*. In certain embodiments, the parasite is *Schistosoma* mansonii. In certain embodiments, the parasite is *Trypanosoma brucei*. In certain embodiments, the parasite is *Trypanosoma cruzi*. In certain embodiments, the parasite is *Toxoplasma gondii*.

In certain embodiments, the ascorbic acid and quinone compounds as used in the methods provided herein are delivered as a single dose such as, e.g., as a single bolus injection, or as a single oral tablet or pill. In certain embodiments, the ascorbic acid and quinone compounds as used in the methods provided herein are administered over time, such as, e.g., continuous infusion over time or divided bolus doses over time.

In certain embodiments, the weight ratio of ascorbic acid compound to the quinone compound as used in the methods provided herein is ranging from about 1 to about 1,000, from about 10 to about 500, from about 50 to about 500, from about 100 to about 500, or from about 200 to about 500. In certain embodiments, the weight ratio of ascorbic acid compound to the quinone compound as used in the methods provided herein is about 100, about 200, about 300, about 400, about 500, or about 600. In certain embodiments, the weight ratio of ascorbic acid compound to the quinone compound as used in the methods provided herein is ranging from 200 to about 400. In certain embodiments, the weight ratio of ascorbic acid compound to the quinone compound as used in the methods provided herein is about 200. In certain embodiments, the weight ratio of ascorbic acid compound to the quinone compound as used in the methods provided herein is about 400.

In certain embodiments, the weight ratio of ascorbic acid compound to the quinone compound as used in the methods provided herein is ranging from about 25 to about 250, or from about 50 to about 200, from about 50 to about 150, or from about 80 to about 120. In certain embodiments, the weight ratio of ascorbic acid compound to the quinone compound as used in the methods provided herein is about 1, about 2, about 4, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, or about 250. In certain embodiments, the weight ratio of ascorbic acid compound to the quinone compound as used in the methods provided herein is about 100. In certain embodiments, the weight ratio of ascorbic acid compound to the quinone compound as used in the methods provided herein is about 200.

In certain embodiments, the ascorbic acid and quinone compounds as used in the methods provided herein are administered once daily (QD), or divided into multiple daily doses such as twice daily (BID), three times daily (TID), four times daily (QID), five times daily, six times daily, seven times daily, eight times daily, nine times daily, or ten times daily. In certain embodiments, the ascorbic acid compound as used in the methods provided herein is administered QD, or divided into multiple daily doses such as BID, TID, QID, five times daily, six times daily, seven times daily, eight times daily, nine times daily, or ten times daily. In certain embodiments, the quinone compound as used in the methods provided herein is administered QD, or divided into multiple daily doses such as BID, TID, QID, five times daily, six times daily, seven times daily, eight times daily, nine times daily, or ten times daily.

In certain embodiments, the ascorbic acid compound and/or the quinone compound as used in the methods provided herein are administered from about 1 to about 20 times a day, from about 1 to about 15 times a day, from about 1 to about 10 times a day, or from about 1 to about 5 times a day. In certain embodiments, the ascorbic acid compound and/or the quinone compound as used in the methods provided herein are administered every 1 to 10 hour(s), every 2 to 8 hours, every 3 to 7 hours, every 4 to 6 hours, or every 5 to 6 hours. In certain embodiments, the ascorbic acid compound and/or the quinone compound as used in the methods provided herein are administered every hour, every 2 hours, every 3 hours, every 4 hours, every 5 hours, every 6 hours, every 7 hours, every 8 hours, every 9 hours, or every 10 hours. In certain embodiments, the ascorbic acid compound and/or the quinone compound as used in the methods provided herein are administered once a day. In certain embodiments, the ascorbic acid compound and/or the quinone compound as used in the methods provided herein are administered 5 times a day. In certain embodiments, the ascorbic acid compound and/or the quinone compound as used in the methods provided herein are administered 10 times a day. In certain embodiments, the ascorbic acid compound and/or the quinone compound as used in the methods provided herein are administered every 4, 5, or 6 hours. In certain embodiments, the ascorbic acid and quinone compounds as used in the methods provided herein are administered daily.

In certain embodiments, the ascorbic acid compound as used in the methods provided herein is administered to the subject in an amount ranging from about 1 to about 1,000 mg/kg/day, from about 5 to about 500 mg/kg/day, or from about 10 to about 100 mg/kg/day. In certain embodiments, the ascorbic acid compound as used in the methods provided herein is administered to the subject in an amount of about 10 mg/kg/day, about 20 mg/kg/day, about 30 mg/kg/day, about 40 mg/kg/day, about 50 mg/kg/day, about 60 mg/kg/day, about 70 mg/kg/day, about 80 mg/kg/day, about 90 mg/kg/day, about 100 mg/kg/day, about 200 mg/kg/day, about 300 mg/kg/day, about 400 mg/kg/day, or about 500 mg/kg/day.

In certain embodiments, the quinone compound as used in the methods provided herein is administered to the subject in an amount ranging from about 0.01 to about 50 mg/kg/day, from about 0.015 to about 50 mg/kg/day, from about 0.05 to about 40 mg/kg/day, from about 0.2 to about 30 mg/kg/day, or from about 10 to about 30 mg/kg/day. In certain embodiments, the quinone compound as used in the methods provided herein is administered to the subject in an amount of about 0.015 mg/kg/day, about 5 mg/kg/day, about 25 mg/kg/day, or about 30 mg/kg/day.

The administered doses of the ascorbic acid and quinone compounds can also each independently be expressed in units other than the unit "mg/kg/day" or "g/kg/day." For example, doses for parenteral administration can be expressed as mg/m$^2$/day. One of ordinary skill in the art would readily know how to convert doses from mg/kg/day to mg/m$^2$/day, given either the height or weight of a subject or both. For example, a dose of 1 mg/kg/day for a 65 kg human is approximately equal to 38 mg/m$^2$/day.

In certain embodiments, the ascorbic acid compound as used in the methods provided herein is administered to the subject in an amount ranging from about 0.1 g to about 3 g every four hours. In certain embodiments, the quinone compound as used in the methods provided herein is administered to the subject in an amount ranging from about 0.2 mg to about 300 mg every four hours.

In certain embodiments, the ascorbic acid compound as used in the methods provided herein is administered to the subject in an amount ranging from about 500 mg to about 3,000 mg a day. In certain embodiments, the quinone compound as used in the methods provided herein is administered to the subject in an amount ranging from about 3 mg to about 30 mg a day. In certain embodiments, the ascorbic acid compound as used in the methods provided herein is administered to the subject in an amount ranging from about 500 mg to about 10,000 mg a day. In certain embodiments, the quinone compound as used in the methods provided herein is administered to the subject in an amount ranging from about 3 mg to about 100 mg a day. In certain embodiments, the ascorbic acid compound as used in the methods provided herein is administered to the subject in an amount of greater than about 500 mg a day. In certain embodiments, the quinone compound as used in the methods provided herein is administered to the subject in an amount of greater than about 3 mg a day. In certain embodiments, the ascorbic acid compound as used in the methods provided herein is administered to the subject in an amount up to about 10,000 mg a day. In certain embodiments, the quinone compound as used in the methods provided herein is administered to the subject in an amount up to about 100 mg a day. In certain embodiments, the ascorbic acid compound as used in the methods provided herein is administered to the subject in an amount up to about 15,000 mg a day. In certain embodiments, the quinone compound as used in the methods provided herein is administered to the subject in an amount up to about 150 mg a day. In certain embodiments, the ascorbic acid compound as used in the methods provided herein is administered to the subject in an amount up to about 20,000 mg a day. In certain embodiments, the quinone compound as used in the methods provided herein is administered to the subject in an amount up to about 200 mg a day. In certain embodiments, the ascorbic acid compound as used in the methods provided herein is administered to the subject in an amount up to about 30,000 mg a day. In certain embodiments, the quinone compound as used in the methods provided herein is administered to the subject in an amount up to about 300 mg a day. In certain embodiments, the ascorbic acid compound as used in the methods provided herein is administered to the subject in an amount up to about 40,000 mg a day. In certain embodiments, the quinone compound as used in the methods provided herein is administered to the subject in an amount up to about 400 mg a day. In certain embodiments, the ascorbic acid compound as used in the methods provided herein is administered to the subject in an amount up to about 50,000 mg a day. In certain embodiments, the quinone compound as used in the methods provided herein is administered to the subject in an amount up to about 500 mg a day. In certain embodiments, the ascorbic acid compound as used in the methods provided herein is administered to the subject in an amount up to about 60,000 mg a day. In certain embodiments, the quinone compound as used in the methods provided herein is administered to the subject in an amount up to about 600 mg a day. In certain embodiments, the ascorbic acid compound as used in the methods provided herein is administered to the subject in an amount up to about 70,000 mg a day. In certain embodiments, the quinone compound as used in the methods provided herein is administered to the subject in an amount up to about 700 mg a day. In certain embodiments, the ascorbic acid compound as used in the methods provided herein is administered to the subject in an amount up to about 80,000 mg a day. In certain embodiments, the quinone compound as used in the methods provided herein is administered to the subject in an amount up to about 800 mg a day. In certain embodiments, the ascorbic acid compound as used in the methods provided herein is administered to the subject in an amount up to about 90,000 mg a day. In certain embodiments, the quinone compound as used in the methods provided herein is administered to the subject in an amount up to about 900 mg a day. In certain embodiments, the ascorbic acid compound as used in the methods provided herein is administered to the subject in an amount up to about 100,000 mg a day. In certain embodiments, the quinone compound as used in the methods provided herein is administered to the subject in an amount up to about 1,000 mg a day. In certain embodiments, the ascorbic acid compound as used in the methods provided herein is administered to the subject in an amount up to about 200,000 mg a day. In certain embodiments, the quinone compound as used in the methods provided herein is administered to the subject in an amount up to about 2,000 mg a day.

In certain embodiments, as used in the methods provided herein, the ascorbic acid compound is administered to the subject in an amount ranging from about 10,000 mg to about 30,000 mg a day; and the quinone compound is administered to the subject in an amount ranging from about 100 mg to about 1,500 mg a day. In certain embodiments, as used in the methods provided herein, the ascorbic acid compound is administered to the subject in an amount ranging from about 10,000 mg to about 20,000 mg a day; and the quinone compound is administered to the subject in an amount ranging from about 100 mg to about 1,000 mg a day. In certain embodiments, as used in the methods provided herein, the ascorbic acid compound is administered to the subject in an amount of about 15,000 mg a day; and the quinone compound is administered to the subject in an amount ranging from about 150 mg to about 600 mg a day. In certain embodiments, as used in the methods provided herein, the ascorbic acid compound is administered to the subject in an amount ranging from about 2,000 mg to about 3,000 mg a day; and the quinone compound is administered to the subject in an amount ranging from about 12 mg to about 19 mg a day. In certain embodiments, as used in the methods provided herein, the ascorbic acid compound is administered to the subject in an amount ranging from about 2,000 mg to about 3,000 mg a day; and the quinone compound is administered to the subject in an amount ranging from about 20 mg to about 30 mg a day. In certain embodiments, as used in the methods provided herein, the ascorbic acid compound is administered to the subject in an amount of about 2,000 mg a day; and the quinone compound is administered to the subject in an amount of about 12 mg a day. In certain embodiments, as used in the methods provided herein, the ascorbic acid compound is administered to the subject in an amount of about 3,000 mg a day; and the quinone compound is administered to the subject in an amount of about 19 mg a day.

In certain embodiments, as used in the methods provided herein, the ascorbic acid compound is administered to the subject in an amount of about 2,000 mg a day; and the quinone compound is administered to the subject in an amount of about 20 mg a day. In certain embodiments, as used in the methods provided herein, the ascorbic acid compound is administered to the subject in an amount of about 3,000 mg a day; and the quinone compound is administered to the subject in an amount of about 30 mg a day.

In certain embodiments, as used in the methods provided herein, the ascorbic acid and quinone compounds are administered as one or more capsules, each comprising about 500 mg of sodium L-ascorbate and about 3 mg of sodium 1,2,3,4-tetrahydro-2-methyl-1,4-dioxo-2-naphthalenesulfonate. In certain embodiments, as used in the methods provided herein, the ascorbic acid and quinone compounds are administered as one or more capsules, each comprising about 500 mg of sodium L-ascorbate and about 5 mg of sodium 1,2,3,4-tetrahydro-2-methyl-1,4-dioxo-2-naphthalenesulfonate.

In certain embodiments, as used in the methods provided herein, the ascorbic acid and quinone compounds are administered as one or more capsules, each comprising about 1,000 mg of calcium L-ascorbate and about 10 mg of 2-methyl-1,4-naphthalenedione. In certain embodiments, as used in the methods provided herein, the ascorbic acid and quinone compounds are administered as one or more capsules, each comprising about 925 mg of calcium L-ascorbate and about 9 mg (e.g., 9.25 mg) of 2-methyl-1,4-naphthalenedione.

Depending on the condition of the parasitic disease to be treated and the subject's condition, the ascorbic acid and quinone compounds used in the methods provided herein can be administered independently by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) route of administration. In certain embodiments, the ascorbic acid and quinone compounds used in the methods provided herein are administered independently by oral, parenteral, intravenous, or topical route of administration. The ascorbic acid and quinone compounds used in the methods provided herein may be formulated, alone or together, in suitable dosage unit with one or more pharmaceutically acceptable excipients appropriate for each route of administration.

In one embodiment, the ascorbic acid compound is administered orally. In another embodiment, the ascorbic acid compound is administered parenterally. In yet another embodiment, the ascorbic acid compound is administered intravenously. In still another embodiment, the ascorbic acid compound is administered topically.

In one embodiment, the quinone compound is administered orally. In another embodiment, the quinone compound is administered parenterally. In yet another embodiment, the quinone compound is administered intravenously. In still another embodiment, the quinone compound is administered topically.

In one embodiment, the ascorbic acid compound is administered concurrently with the quinone compound. In another embodiment, the ascorbic acid compound is administered separately with the quinone compound. In yet another embodiment, the ascorbic acid compound is administered sequentially with the quinone compound. In yet another embodiment, the ascorbic acid compound is administered before the quinone compound. In yet another embodiment, the ascorbic acid compound is administered after the quinone compound.

In certain embodiments, the ascorbic acid and quinone compounds are administered together in a single composition comprising ascorbic acid, or a single enantiomer, a mixture of enantiomers, or a mixture of diastereomers thereof; or a pharmaceutically acceptable salt, solvate, or hydrate thereof; and a quinone compound, or a single enantiomer, a mixture of enantiomers, or a mixture of diastereomers thereof, or a pharmaceutically acceptable salt, solvate, hydrate, or prodrug thereof.

In certain embodiments, the ascorbic acid and quinone compounds are administered to the subject after mealtime. In certain embodiments, the ascorbic acid and quinone compounds are administered to the subject with a meal.

In one embodiment, the antiparasitic agent is an antiprotozoal, an antihelminthic, an antinematode, an anticestode, an antitrematode, an antiamoebic, or an antifungal. In another embodiment, the antiparasitic agent is albendazole, amphotericin B, benznidazole, bephenium, diethylcarbamzine, eflornithine, flubendazole, ivermectin, mebendazole, meglumine antimonite, melarsoprol, metronidazole, miltefosine, niclosamide, nifurtimox, nitazoxanide, pentavalent antimony, praziquantel, pyrantel, pyrvinium, sodium stibogluconate, thiabendazole, or tinidazole. In yet another embodiment, the antiparasitic agent is nifurtimox.

In one embodiment, the antiparasitic agent is a nitroimidazole. In another embodiment, the antiparasitic agent is a 2-nitroimidazole. In yet another embodiment, the antiparasitic agent is a 5-nitroimidazole. In yet another embodiment, the antiparasitic agent is azanidazole, dimetridazole, megazol, metronidazole, nimorazole, ornidazole, pretomanid, or tinidazole. In still another embodiment, the antiparasitic agent is benznidazole.

In certain embodiments, the subtherapeutically effective amount of the antiparasitic agent is no greater than about 1/2, no greater than about 1/3, no greater than about 1/4, no greater than about 1/5, no greater than about 1/10, no greater than about 1/20, no greater than about 1/50, or no greater than about 1/100 of the therapeutically effective amount of the antiparasitic agent when used alone.

In certain embodiments, the subtherapeutically effective amount of the antiparasitic agent is no greater than about 1/2 of the therapeutically effective amount of the antiparasitic agent when used alone. In certain embodiments, the subtherapeutically effective amount of the antiparasitic agent is no greater than about 1/3 of the therapeutically effective amount of the antiparasitic agent when used alone. In certain embodiments, the subtherapeutically effective amount of the antiparasitic agent is no greater than about 1/4 of the therapeutically effective amount of the antiparasitic agent when used alone. In certain embodiments, the subtherapeutically effective amount of the antiparasitic agent is no greater than about 1/5 of the therapeutically effective amount of the antiparasitic agent when used alone. In certain embodiments, the subtherapeutically effective amount of the antiparasitic agent is no greater than about 1/10 of the therapeutically effective amount of the antiparasitic agent when used alone. In certain embodiments, the subtherapeutically effective amount of the antiparasitic agent is no greater than about 1/20 of the therapeutically effective amount of the antiparasitic agent when used alone. In certain embodiments, the subtherapeutically effective amount of the antiparasitic agent is no greater than about 1/50 of the therapeutically effective amount of the antiparasitic agent when used alone. In certain embodiments, the subtherapeutically effective amount of the antiparasitic agent is no greater than about 1/100 of the therapeutically effective amount of the antiparasitic agent when used alone.

In certain embodiments, the antiparasitic agent is administered to the subject before the administration of the ascorbic acid and quinone compounds. In certain embodiments, the antiparasitic agent is administered to the subject concurrently with the ascorbic acid and quinone compounds. In certain embodiments, the antiparasitic agent is administered to the subject after the administration of the ascorbic acid and quinone compounds.

In certain embodiments, the antiparasitic agent as used in the methods provided herein is administered QD, or divided into multiple daily doses such as BID, TID, or QID. In certain embodiments, the antiparasitic agent as used in the methods provided herein is administered QD. In certain embodiments, the antiparasitic agent as used in the methods provided herein is administered BID. In certain embodiments, the antiparasitic agent as used in the methods provided herein is administered TID. In certain embodiments, the antiparasitic agent as used in the methods provided herein is administered QID.

In certain embodiments, the antiparasitic agent as used in the methods provided herein is administered to the subject in an amount ranging from about 10 μg/kg/day to about 10 mg/kg/day, from about 20 μg/kg/day to about 5 mg/kg/day, from about 50 μg/kg/day to about 2 mg/kg/day, or from about 100 μg/kg/day to about 1 mg/kg/day. In certain embodiments, the antiparasitic agent as used in the methods provided herein is administered to the subject in an amount ranging from about 10 μg/kg/day to about 10 mg/kg/day. In certain embodiments, the antiparasitic agent as used in the methods provided herein is administered to the subject in an amount ranging from about 20 μg/kg/day to about 5 mg/kg/day. In certain embodiments, the antiparasitic agent as used in the methods provided herein is administered to the subject in an amount ranging from about 50 μg/kg/day to about 2 mg/kg/day. In certain embodiments, the antiparasitic agent as used in the methods provided herein is administered to the subject in an amount ranging from about 100 μg/kg/day to about 1 mg/kg/day.

In certain embodiments, the antiparasitic agent is benznidazole administered to the subject in an amount ranging from about 10 μg/kg/day to about 10 mg/kg/day, from about 20 μg/kg/day to about 5 mg/kg/day, from about 50 μg/kg/day to about 2 mg/kg/day, or from about 100 μg/kg/day to about 1 mg/kg/day. In certain embodiments, the antiparasitic agent is benznidazole administered to the subject in an amount ranging from about 10 μg/kg/day to about 10 mg/kg/day. In certain embodiments, the antiparasitic agent is benznidazole administered to the subject in an amount ranging from about 20 μg/kg/day to about 5 mg/kg/day. In certain embodiments, the antiparasitic agent is benznidazole administered to the subject in an amount ranging from about 50 μg/kg/day to about 2 mg/kg/day. In certain embodiments, the antiparasitic agent is benznidazole administered to the subject in an amount ranging from about 100 μg/kg/day to about 1 mg/kg/day.

The administered doses of the antiparasitic agent can also be expressed in units other than the unit "mg/kg/day" or "g/kg/day." For example, doses for parenteral administration can be expressed as mg/m²/day. One of ordinary skill in the art would readily know how to convert doses from mg/kg/day to mg/m²/day, given either the height or weight of a subject or both. For example, a dose of 1 mg/kg/day for a 65 kg human is approximately equal to 38 mg/m²/day.

In certain embodiments, the antiparasitic agent as used in the methods provided herein is administered to the subject in an amount ranging from about 0.01 mg to about 200 mg per day, from about 0.02 mg to about 100 mg per day, from about 0.05 mg to about 50 mg per day, from about 0.1 mg to about 10 mg per day, from about 0.1 mg to about 5 mg per day, from about 0.1 mg to about 2 mg per day, or from about 0.1 mg to about 1 mg per day. In certain embodiments, the antiparasitic agent as used in the methods provided herein is administered to the subject in an amount ranging from about 0.01 mg to about 200 mg per day. In certain embodiments, the antiparasitic agent as used in the methods provided herein is administered to the subject in an amount ranging from about 0.02 mg to about 100 mg per day. In certain embodiments, the antiparasitic agent as used in the methods provided herein is administered to the subject in an amount ranging from about 0.05 mg to about 50 mg per day. In certain embodiments, the antiparasitic agent as used in the methods provided herein is administered to the subject in an amount ranging from about 0.1 mg to about 10 mg per day. In certain embodiments, the antiparasitic agent as used in the methods provided herein is administered to the subject in an amount ranging from about 0.1 mg to about 5 mg per day. In certain embodiments, the antiparasitic agent as used in the methods provided herein is administered to the subject in an amount ranging from about 0.1 mg to about 2 mg per day. In certain embodiments, the antiparasitic agent as used in the methods provided herein is administered to the subject in an amount ranging from about 0.1 mg to about 1 mg per day.

In certain embodiments, the antiparasitic agent is benznidazole administered to the subject in an amount ranging from about 0.01 mg to about 200 mg per day, from about 0.02 mg to about 100 mg per day, from about 0.05 mg to about 50 mg per day, from about 0.1 mg to about 10 mg per day, from about 0.1 mg to about 5 mg per day, from about 0.1 mg to about 2 mg per day, or from about 0.1 mg to about 1 mg per day. In certain embodiments, the antiparasitic agent is benznidazole administered to the subject in an amount ranging from about 0.01 mg to about 200 mg per day. In certain embodiments, the antiparasitic agent is benznidazole administered to the subject in an amount ranging from about 0.02 mg to about 100 mg per day. In certain embodiments, the antiparasitic agent is benznidazole administered to the subject in an amount ranging from about 0.05 mg to about 50 mg per day. In certain embodiments, the antiparasitic agent is benznidazole administered to the subject in an amount ranging from about 0.1 mg to about 10 mg per day. In certain embodiments, the antiparasitic agent is benznidazole administered to the subject in an amount ranging from about 0.1 mg to about 5 mg per day. In certain embodiments, the antiparasitic agent is benznidazole administered to the subject in an amount ranging from about 0.1 mg to about 2 mg per day. In certain embodiments, the antiparasitic agent is benznidazole administered to the subject in an amount ranging from about 0.1 mg to about 1 mg per day.

Depending on the condition of the parasitic disease to be treated and the subject's condition, the antiparasitic agent used in the methods provided herein can be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) route of administration. In certain embodiments, the antiparasitic agent used in the methods provided herein is administered by oral, parenteral, intravenous, or topical route of administration. The antiparasitic agent used in the methods provided herein may be formulated, alone or together, in suitable dosage unit with one or more pharmaceutically acceptable excipients appropriate for each route of administration.

In one embodiment, the antiparasitic agent is administered orally. In another embodiment, the antiparasitic agent is administered parenterally. In yet another embodiment, the antiparasitic agent is administered intravenously. In still another embodiment, the antiparasitic agent is administered topically.

The routes of administration of the ascorbic acid compound, the quinone compound, and the antiparasitic agent can be the same or different.

In certain embodiments, the ascorbic acid compound, the quinone compound, and the antiparasitic agent are administered repetitively if necessary, for example, until the subject experiences stable disease or regression, or until the subject experiences disease progression or unacceptable toxicity. Stable disease or lack thereof is determined by methods known in the art such as evaluation of subject's symptoms, physical examination, or diagnostic testing. In certain embodiments, the ascorbic acid compound, the quinone compound, and the antiparasitic agent are administered repetitively until the subject becomes immunoglobulin G (IgG) antibody negative agonist a recombinant antigen of the parasite. In certain embodiments, the ascorbic acid compound, the quinone compound, and the antiparasitic agent are administered repetitively until the subject becomes immunoglobulin G (IgG) antibody negative agonist a recombinant antigen of *Trypanosoma*. In certain embodiments, the ascorbic acid compound, the quinone compound, and the antiparasitic agent are administered repetitively until the subject becomes immunoglobulin G (IgG) antibody negative agonist a recombinant antigen of *Trypanosoma cruzi*.

In certain embodiments, the ascorbic acid compound, the quinone compound, and the antiparasitic agent are administered to the subject over an extended period of time, ranging from about 10 day to about 5 years, from about 20 days to about 2 years, from about 20 days to about 1 years, from about 20 days to about 6 months, from about 20 days to about 90 days, or from about 30 days to about 60 days.

In certain embodiments, the ascorbic acid compound, the quinone compound, and the antiparasitic agent as used in the methods provided herein are cyclically administered. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

In certain embodiments, the methods provided herein encompass treating a subject regardless of patient's age. In certain embodiments, the subject is a pediatric patient. In certain embodiments, the subject is a pediatric patient of 2 to 12 years.

In certain embodiments, the subject is a mammal. In certain embodiments, the mammal is a human. In certain embodiments, the subject is one of livestock. In certain embodiments, the subject is a domesticated animal.

In certain embodiments, the ascorbic acid compound, the quinone compound, and the antiparasitic agent act synergistically in treating, preventing, or alleviating one or more symptoms of the parasitic disease when compared to the administration of the ascorbic acid compound, the quinone compound, or the antiparasitic agent alone.

Without being limited by any theory, a synergistic effect of the combination of the active ingredients provided herein permits the use of lower dosages of at least one of the active ingredients, and/or less frequent administration of the combination to a subject for treating the parasitic disease. The ability to utilize lower dosages of certain active ingredients in the combination (e.g., a prophylactic or therapeutic agent) and/or to administer the combination less frequently reduces the toxicity associated with the administration of the combination to a subject without reducing the efficacy of the combination in the prevention or treatment of the parasitic disease. In addition, a synergistic effect can result in improved efficacy of the active ingredients in the prevention or treatment of the parasitic disease. Furthermore, a synergistic effect of the combination may avoid or reduce adverse or unwanted side effects associated with the use of at least one of the active ingredients.

In one embodiment, provided herein is a method of inhibiting parasitic growth, comprising contacting a parasite with: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

In another embodiment, provided herein is a method of killing a parasite, comprising contacting the parasite with: (a) a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof; and (b) a subtherapeutically effective amount of an antiparasitic agent.

In yet another embodiment, provided herein is a method of increasing the cytotoxicity of an antiparasitic agent to a parasite, comprising contacting the parasite with a therapeutically effective amount of: (i) ascorbic acid, or a single enantiomer, a mixture of enantiomers, or a mixture of diastereomers thereof; or a pharmaceutically acceptable salt, solvate, or hydrate thereof; and (ii) a quinone compound, or a single enantiomer, a mixture of enantiomers, or a mixture of diastereomers thereof, or a pharmaceutically acceptable salt, solvate, hydrate, or prodrug thereof.

In certain embodiments, the methods provided herein further comprise administering an additional therapeutic agent or therapy that is useful in treating, preventing, or ameliorating one or more symptoms of a parasitic disease. Effective dosages of the additional therapeutic agent can be administered together with, alternatively to, or sequentially to the administration of the active ingredients provided herein. The dosages given will depend on absorption, inactivation, and excretion rates of the therapeutic agents as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In certain embodiments, provided herein are kits which, when used by the medical practitioner, can simplify the administration of appropriate amounts of active ingredients to a subject. In certain embodiments, the kit provided herein includes containers and dosage forms of the active ingredients provided herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

Example 1

Evaluation of Vitamins C and $K_3$ in Combination with an Antiparasitic Agent in Mice Infected with *Trypanosoma cruzi*

Male BALB/c mice (approximately 7-8 weeks) were infected intraperitoneally with $10^4$ parasites per mouse. Treatment started 24 hours after infection. The administration of vitamin C (i.e., L-ascorbic acid), vitamin $K_3$ (i.e., 2-methyl-1,4-naphthoquinone or menadione), APATONE®, and benznidazole, alone or in combination, were administered once a day orally in different concentrations.

The mice were divided into the following groups and each group contained seven mice:
i. infected and not treated;
ii. infected and treated with 200 mg/kg of vitamin C;
iii. infected and treated with 3.5 mg/kg of vitamin $K_3$;
iv. infected and treated with APATONE® (200 mg/kg of vitamin C and 3.5 mg/kg of vitamin $K_3$);
v. infected and treated with APATONE® (200 mg/kg of vitamin C and 3.5 mg/kg of vitamin $K_3$) plus 5 mg/kg benznidazole;
vi. infected and treated with benznidazole at 5 mg/kg;
vii. infected and treated with benznidazole at 100 mg/kg; and
viii. not infected and not treated.

Parasitemia levels were individually checked every day starting from 3 days postinfection (dpi) over a 21-day period by direct microscopic analysis of 5 μL blood drawn by puncture of the tail tip of each mouse. The parasites present in 50 fields were counted in 40× objective. Mortality was checked daily until 21 dpi and was expressed as a percentage of survival. All assays were carried out after the approval of the Ethical Conduct on the use of Animals in Experiments (CEAE) of UE111, protocol number CEUA 6642060717.

As shown in FIG. 1, APATONE® decreased parasitemia levels compared to the infected and untreated group (Group i). This reduction in parasitemal peak (8 dpi) was 77%. At the end of the 21 dpi, no trypomastigotes were observed in the bloodstream of APATONE®-treated mice. The mice treated with APATONE® plus benznidazole (5 mg/kg) in combination completely eliminated parasites from the bloodstream, even from the beginning of the infection. In view of the superior and unexpected results obtained with this treatment, three mice from Group v were kept for another 15 days to verify if the parasitemia would return after ending the treatment. During these 15 days, no parasite has been observed in the bloodstream and all the three mice survived (FIG. 2).

The mice treated only with vitamin C or vitamin $K_3$ alone died from day 14, showing that the vitamins alone did not have any efficacy. The amount of parasites observed in the bloodstream of these nice was similar to the infected and untreated control. Three mice died in group treated only with benznidazole at 5 mg/kg, a concentration that is known to be not effective, only 4 mice remained. The amount of parasites observed in the bloodstream of this group (Group vi) was also similar to the infected and untreated control, confirming that benznidazole at 5 mg/kg is not effective to eliminate parasites. No mice died and no parasite was observed in the bloodstream in the group treated with benznidazole at 100 mg/kg, the effective concentration however known to induce severe toxic effects (FIG. 1).

Figure 2:
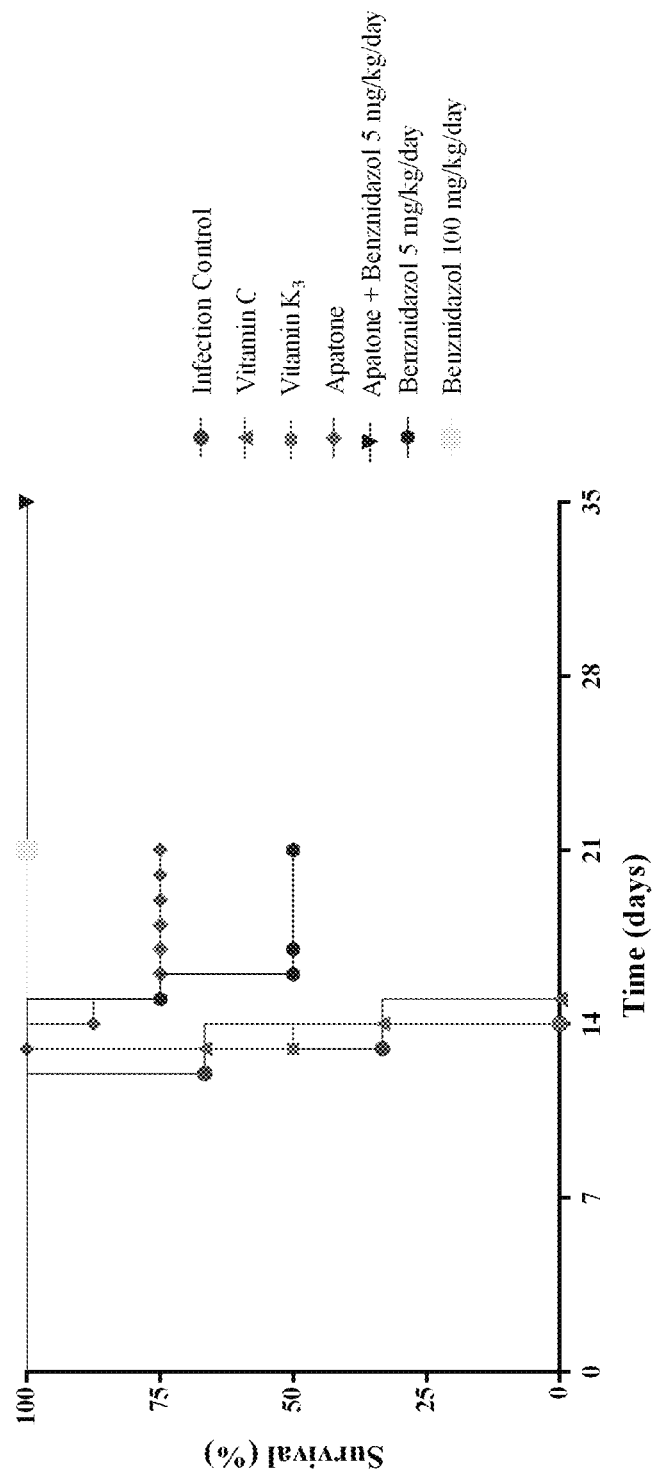
FIG. 2 shows the effects of vitamin C, vitamin $K_3$, APATONE®, and benznidazole on the survival rates of mice with acute *Chagas disease* infection in a murine model.

At the end of 21 dpi, the infected and treated group with APATONE® had a survival rate of 77%, while the group treated with APATONE® and benznidazole (5 mg/kg) in combination presented 100% survival (FIG. 2). The mice infected and treated with APATONE® and treated with combination of APATONE® plus benznidazole presented similar appearance to the mice in the not infected and not treated group.

Cytokine analysis was performed on the mice infected with *T. cruzi*. A cytokine bead (CBA) kit was used to quantify the levels of Th1 cytokines (IL-2, TNF-α, and INF-γ), Th2 (IL-4, IL-5, and IL-10A), and Th17 (IL-17) by flow cytometry. Seven bead populations with different fluorescence intensities were conjugated to a specific capture antibody for each cytokine, mixed to the CBA and read without FL3 channel of a FACSCalibur flow cytometer. The populations of beads were visualized according to their respective fluorescence intensities: from less bright to brighter.

Acquisition tubes were prepared with: 50 μL of a sample, 50 μL of beads, and 50 μL of Th1/Th2/Th17 PE (Mouse Th1/Th2/Th17 PE Detection Reagent/1 vial, 4 mL). The same procedure was performed to obtain a standard curve. The samples in the tubes were homogenized and incubated for three hours at room temperature in dark. The data acquisition and analysis were performed using a FACSCalibur flow cytometer equipped with a CellQuest software.

Figure 3:
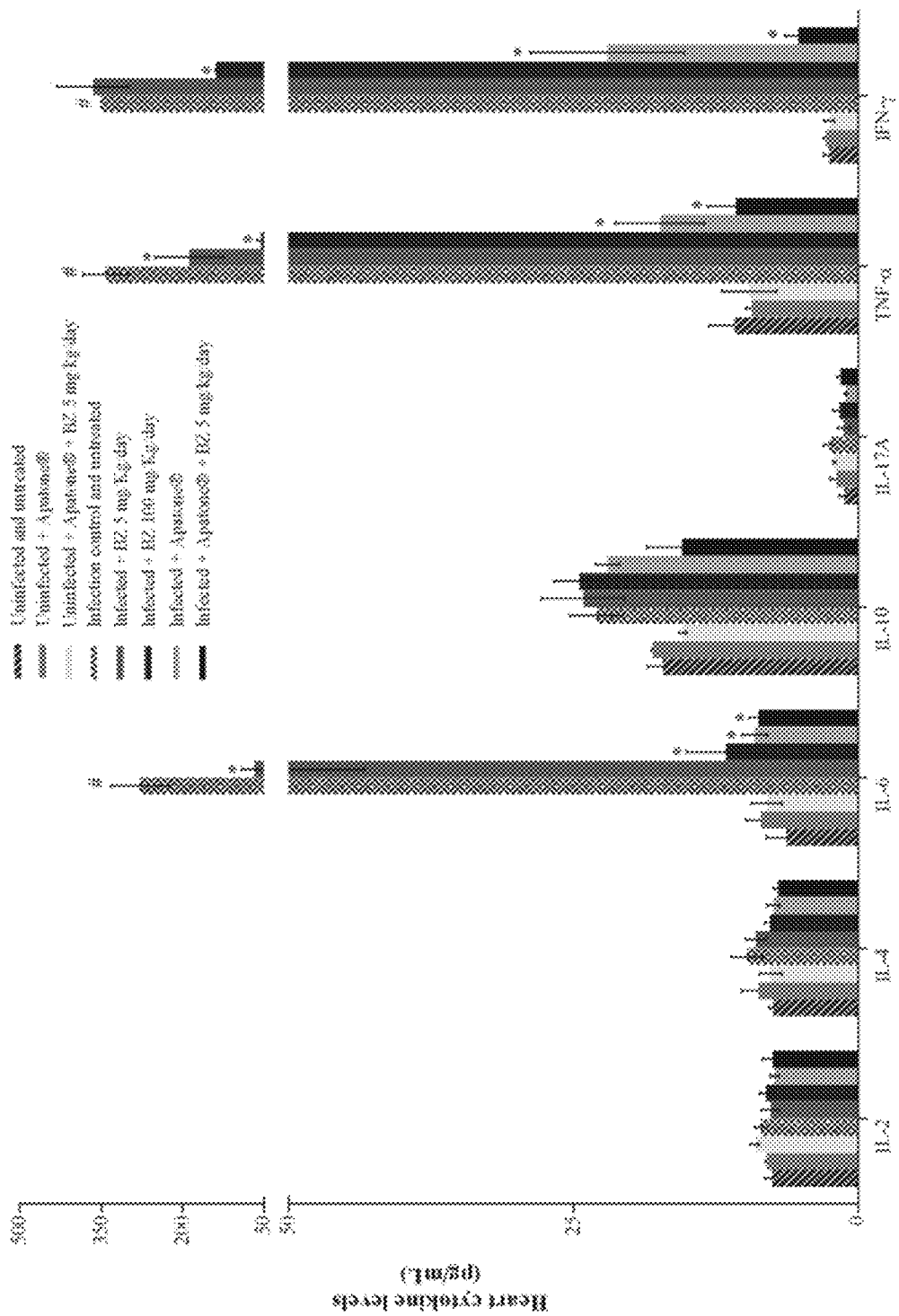
FIG. 3 shows the effects of vitamin C, vitamin $K_3$, APATONE®, and benznidazole on heart cytokine levels in a murine model of *Chagas disease*, where the symbol * indicates a significant difference compared with the control group ($p \leq 0.05$).
Figure 4:
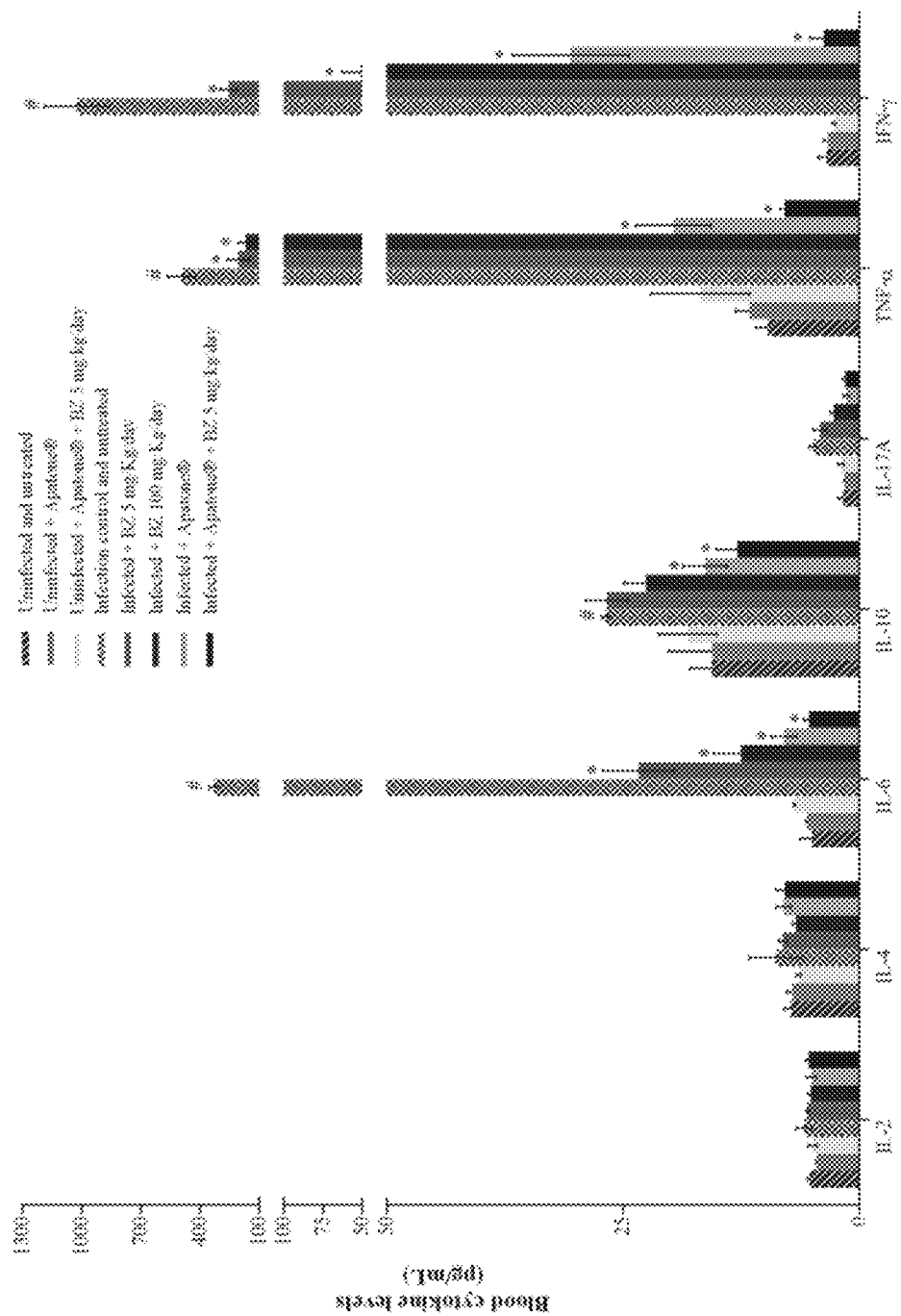
FIG. 4 shows the effects of vitamin C, vitamin $K_3$, APATONE®, and benznidazole on blood cytokine levels in a murine model of *Chagas disease*, where the symbol * indicates a significant difference compared with the control group ($p \leq 0.05$).

The levels of proinflammatory (IL-6, TNF-α, INF-γ, IL-2, and IL-17) and anti-inflammatory cytokines (IL-4 and IL-10) in heart (FIG. 3) in blood were determined on the mice infected with *T. cruzi*. FIG. 3 shows that the mice infected with *T. cruzi* and untreated had significant and high levels of IL-6, TNF-α, and IFN-γ (up to 15.3; 30.5; and 135.5 fold, respectively) compared with the uninfected and untreated mice. The mice infected with *T. cruzi* and treated with benznidazole at 5 mg and 100 mg showed a significant decrease in the levels of IL-6 and TNF-α, compared with the infected and untreated group. However, the levels of IL-6 and TNF-α in this group were still high compared with the uninfected and untreated group. It is important to remember that the treatment with benznidazole (5 mg) did not decrease the amount of parasites in the bloodstream as in the infected and untreated group (FIG. 1). Thus, it is likely that the high levels of IL-6 and TNF-α in the mice infected with *T. cruzi* and treated with benznidazole (5 mg) are related to the inflammatory process induced by the parasite in the bloodstream. On the other hand, in the mice treated with benznidazole at 100 mg (the effective concentration), there was no parasite detected in the bloodstream (FIG. 1). Thus, it is likely that the high levels of IL-6 and TNF-α in the mice infected with *T. cruzi* and treated with benznidazole (100 mg) are related to the proinflammatory activity of benznidazole (a side effect). However, the mice infected with *T. cruzi* and treated with APATONE® and benznidazole (5 mg/kg/day) in combination showed a marked and significant decrease in the levels of IL-6, TNF-α, and IFN-γ (up to 30.8; 30.7; and 65.7 fold; respectively), compared to the infected and untreated group. The levels of IL-6, TNF-α, and IFN-γ in the group treated with APATONE® and benznidazole (5 mg/kg/day) in combination are similar to the levels of IL-6, TNF-α and IFN-γ in the uninfected and untreated group. The mice infected with *T. cruzi* and treated only with APATONE® also significantly decrease the levels of pro-inflammatory cytokines (IL-6, TNF-α, and IFN-γ) (up to 29.7; 18.6; and 15.0 fold; respectively), compared with the infected and untreated group, however the decreases in the levels of TNF-α and IFN-γ were not as significant as the combination of APATONE® and benznidazole (5 mg). FIG. 4 shows that the blood cytokine levels are very similar to the heart cytokine levels in *T. cruzi* infected mice.

Real-time quantitative PCR (RT-qPCR) was performed to determine tissue parasite burden in control mice and *T. cruzi*-infected and treated mice. Heart tissues were collected from mice at 21 dpi, weighed, and washed in PBS. The DNAs were purified by PureLink Genomic kit. The DNAs Real-time PCR was performed by using QuantiNova SYBR green PCR Kit with 100 ng of total genomic DNA (gDNA). The primers used were TCZ-F (5'-GCTCTTGCC-CACAMGGGTGC-3') and TCZ-R (5'-CCAAGCAGCG-GATA-GTTCAGG-3').

The samples were amplified with a LIGHTCYCLER® 480 under the following PCR conditions: a denaturation phase at 95° C. for 2 min, then 35 cycles of amplification 95° C. for 15 s, 60° C. for 10 s. At the end of each run, a melting curve was obtained from 65° C. to 97° C. to monitor primer dimers or non-specific product formation. A standard curve was established using purified *T. cruzi* DNA; serial dilutions ranging from 100 to 0.001 ng of DNA parasites in triplicate. The standard curve was generated by LIGHTCYCLER®96 software and used to calculate the parasite level in each sample. The parasite levels were based on DNA per epimastigote cell, where DNA per cell was considered 200 fg/parasite.

Figure 5:
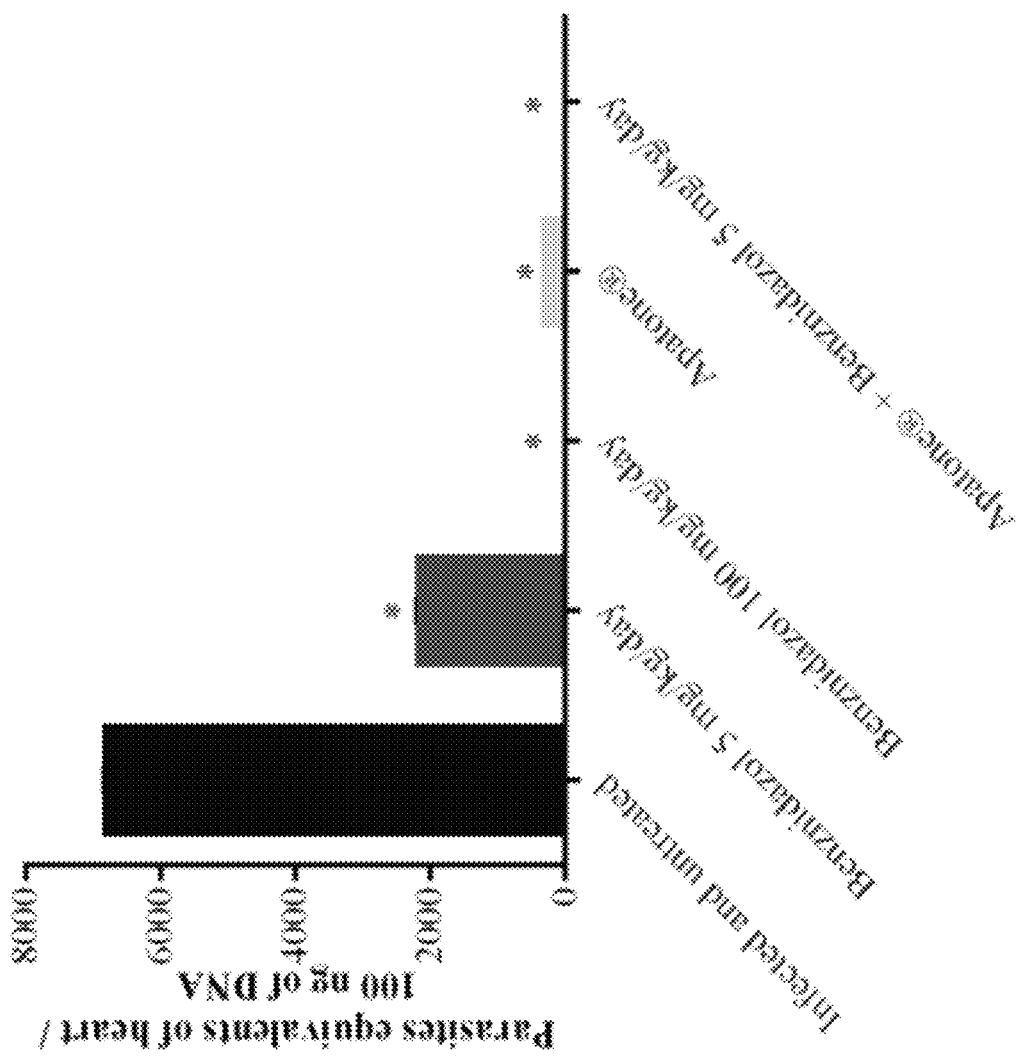
FIG. 5 shows the effects of vitamin C, vitamin $K_3$, APATONE®, and benznidazole on parasite burdens in cardiac tissues in a murine model of *Chagas disease*, where the symbol * indicates a significant difference compared with the control group ($p \leq 0.05$).
Figure 6:
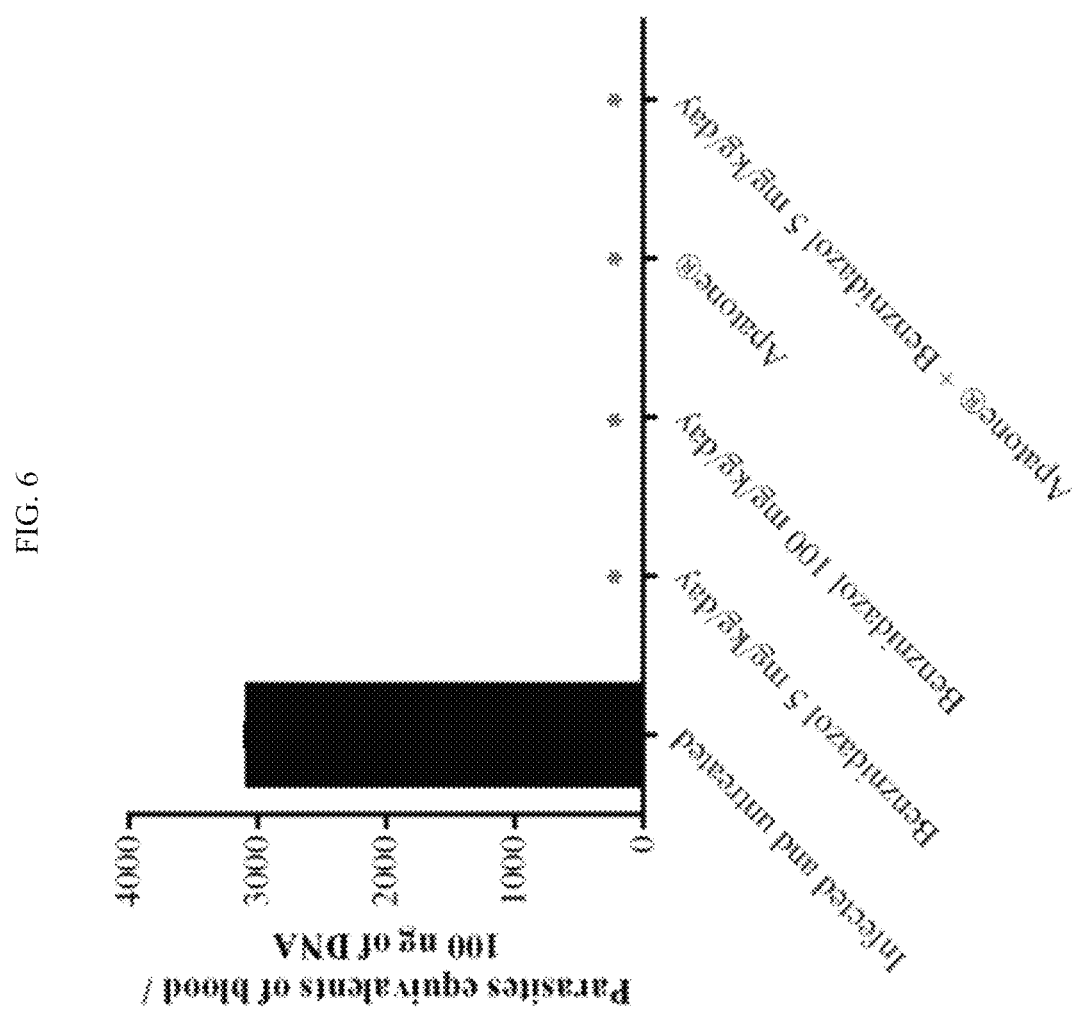
FIG. 6 shows the effects of vitamin C, vitamin $K_3$, APATONE®, and benznidazole on parasite burdens in blood in a murine model of *Chagas disease*, where the symbol * indicates a significant difference compared with the control group ($p \leq 0.05$).

The group treated with APATONE® and benznidazole (5 mg) in combination had complete elimination of parasites from the cardiac tissues (FIG. 5) and bloodstream (FIG. 6). The group treated with APATONE® had a significant reduction in the parasite burden in cardiac tissues (FIG. 5) and a complete elimination of the parasites from the bloodstream (FIG. 6) compared with the infected and untreated group.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating or alleviating one or more symptoms of a parasitic disease in a subject, comprising administering to the subject: (i) ascorbic acid, or a single enantiomer, a mixture of enantiomers, or a mixture of diastereomers thereof; or a pharmaceutically acceptable salt thereof; (ii) a quinone compound, or a single enantiomer, a mixture of enantiomers, or a mixture of diastereomers thereof; or a pharmaceutically acceptable salt thereof; and (iii) an antiparasitic agent.

2. The method of claim 1, wherein the parasitic disease is African trypanosomiasis, amoebiasis, ascariasis, babesiosis, Chagas disease, cryptosporidiosis, cutaneous larva migrans, dirofilariasis, echinococcosis, fasciolosis, filariasis, lymphatic filariasis, giardiasis, helminthiasis, hookworm infection, leishmaniasis, visceral leishmaniasis, malaria, neurocysticercosis, onchocerciasis, protozoan infection, schistosomiasis, taeniasis, tapeworm infection, toxocariasis, toxoplasmosis, trichinosis, or zoonosis.

3. The method of claim 1, wherein the parasitic disease is Chagas disease.

4. The method of claim 1, wherein the parasitic disease is leishmaniasis.

5. The method of claim 1, wherein the parasitic disease is cutaneous leishmaniasis, mucocutaneous leishmaniasis, or visceral leishmaniasis.

6. A method of inhibiting parasitic growth in, eliminating a parasite from, or increasing the quality of life of a subject infected with a parasite, comprising administering to the subject: (i) ascorbic acid, or a single enantiomer, a mixture of enantiomers, or a mixture of diastereomers thereof; or a pharmaceutically acceptable salt, solvate, or hydrate thereof; (ii) a quinone compound, or a single enantiomer, a mixture of enantiomers, or a mixture of diastereomers thereof; or a pharmaceutically acceptable salt thereof; and (iii) an antiparasitic agent.

7. A method of increasing the efficacy of an antiparasitic agent in, increasing tolerance to an antiparasitic agent in, reducing a side effect of an antiparasitic agent to, or reducing a toxicity of an antiparasitic agent to a subject infected with a parasite, comprising administering to the subject: (i) ascorbic acid, or a single enantiomer, a mixture of enantiomers, or a mixture of diastereomers thereof; or a pharmaceutically acceptable salt; and (ii) a quinone compound, or a single enantiomer, a mixture of enantiomers, or a mixture of diastereomers thereof; or a pharmaceutically acceptable salt thereof.

8. The method of claim 1, wherein the ascorbic acid is L-ascorbic acid or a pharmaceutically acceptable salt thereof.

9. The method of claim 8, wherein the ascorbic acid is an alkali or alkaline earth metal salt of L-ascorbic acid.

10. The method of claim 8, wherein the ascorbic acid is sodium L-ascorbate, potassium L-ascorbate, calcium L-ascorbate, or magnesium L-ascorbate.

11. The method of claim 1, wherein the quinone compound is vitamin $K_3$.

12. The method of claim 11, wherein vitamin $K_3$ is 1,2,3,4-tetrahydro-2-methyl-1,4-dioxo-2-naphthalenesulfonic acid or a pharmaceutically acceptable salt thereof.

13. The method of claim 11, wherein vitamin K3 is an alkali or alkaline earth metal salt of 1,2,3,4-tetrahydro-2-methyl-1,4-dioxo-2-naphthalenesulfonic acid.

14. The method of claim 11, wherein vitamin $K_3$ is 2-methyl-1,4-naphthalenedione.

15. The method of claim 1, wherein the molar ratio of the ascorbic acid to the quinone compound is ranging from about 50 to about 500.

16. The method of claim 1, wherein the ascorbic acid is administered in an amount ranging from about 500 mg to about 30,000 mg per day, and the quinone compound is administered in an amount ranging from about 3 mg to about 1,200 mg per day.

17. The method of claim 1, wherein the ascorbic acid and the quinone compound are administered as one or more capsules, each comprising about 500 mg of sodium L-ascorbate and about 3 mg of sodium 1,2,3,4-tetrahydro-2-methyl-1,4-dioxo-2-naphthalenesulfonate.

18. The method of claim 1, wherein the ascorbic acid and the quinone compound are administered as one or more capsules, each comprising about 1,000 mg of calcium L-ascorbate and about 10 mg of 2-methyl-1,4-naphthalenedione.

19. The method of claim 1, wherein the antiparasitic agent is an antiprotozoal, an antihelminthic, an antinematode, an anticestode, an antitrematode, an antiamoebic, or an antifungal.

20. The method of claim 1, wherein the antiparasitic agent is albendazole, amphotericin B, benznidazole, bephenium, diethylcarbamzine, eflornithine, flubendazole, ivermectin, mebendazole, meglumine antimonite, melarsoprol, metronidazole, miltefosine, niclosamide, nifurtimox, nitazoxanide, pentavalent antimony, praziquantel, pyrantel, pyrvinium, sodium stibogluconate, thiabendazole, or tinidazole.

* * * * *